United States Patent
Kim et al.

(10) Patent No.: US 12,060,560 B2
(45) Date of Patent: Aug. 13, 2024

(54) INSULIN RECEPTOR APTAMER AND PHARMACEUTICAL COMPOSITION FOR TREATING DIABETES COMPRISING THE SAME

(71) Applicant: APTAMER SCIENCES INC., Gyeongsangbukdo (KR)

(72) Inventors: Youndong Kim, Gyeonggi-do (KR); Jo Woon Yi Lee, Gyeonggi-do (KR); Solip Choi, Gyeonggi-do (KR); So Ryong Lim, Gyeonggi-do (KR); Sung Ho Ryu, Gyeongsangbuk-do (KR); Na-Oh Yunn, Chungcheongnam-do (KR)

(73) Assignee: APTAMER SCIENCES INC. (KR)

( * ) Notice: Subject to any disclaimer, the term of this patent is extended or adjusted under 35 U.S.C. 154(b) by 91 days.

(21) Appl. No.: 16/640,343

(22) PCT Filed: May 10, 2018

(86) PCT No.: PCT/KR2018/005400
§ 371 (c)(1),
(2) Date: Feb. 19, 2020

(87) PCT Pub. No.: WO2019/216458
PCT Pub. Date: Nov. 14, 2019

(65) Prior Publication Data
US 2023/0159934 A1    May 25, 2023

(51) Int. Cl.
*C12N 15/115* (2010.01)
*A61K 31/7115* (2006.01)
*A61P 3/10* (2006.01)

(52) U.S. Cl.
CPC ........ *C12N 15/115* (2013.01); *A61K 31/7115* (2013.01); *A61P 3/10* (2018.01); *C12N 2310/16* (2013.01); *C12N 2310/335* (2013.01); *C12N 2310/3525* (2013.01)

(58) Field of Classification Search
None
See application file for complete search history.

(56) References Cited

FOREIGN PATENT DOCUMENTS

| JP | 2009-183192 A | 8/2009 |
|---|---|---|
| KR | 10-2017-0013178 A | 7/2018 |

OTHER PUBLICATIONS

Chang, M. et al, 'Aptamer-based single-molecule imaging of insulin receptors in living cells.', J. Biomed. Opt., May 2014, 19, 5, 051204.
Aboni, M. et al, 'Targeting Insulin Receptor with a Novel Internalizing Aptamer.', Mol. Ther. Nucleic Acids., Sep. 20, 2016, 5, 9, e365.
Yunn, N. O. et al, 'Agonistic aptamer to the insulin receptor leads to biased signaling and functional selectivity through allosteric modulation.', Nucleic Acids Res., 2015, 43, 16, pp. 7688-7701.

*Primary Examiner* — Ekaterina Poliakova-Georgantas
*Assistant Examiner* — Ekaterina Poliakova
(74) *Attorney, Agent, or Firm* — Gavrilovich, Dodd & Lindsey LLP

(57) ABSTRACT

Provided is a DNA aptamer specifically binding to an insulin receptor, a pharmaceutical composition for treating diabetes including the same, and a composition for diagnosing diabetes including the DNA aptamer.
The insulin receptor aptamer may be effectively used in compositions for preventing or treating insulin-related diseases due to better downstream signaling activity of the insulin receptor than insulin or existing insulin receptor aptamers conventionally used for treatment of insulin-related diseases such as diabetes.

19 Claims, 12 Drawing Sheets
Specification includes a Sequence Listing.

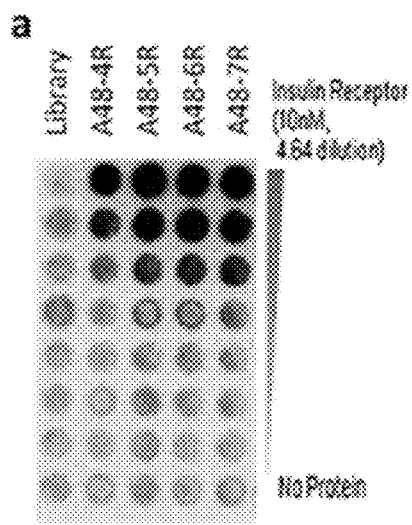
FIG. 2A
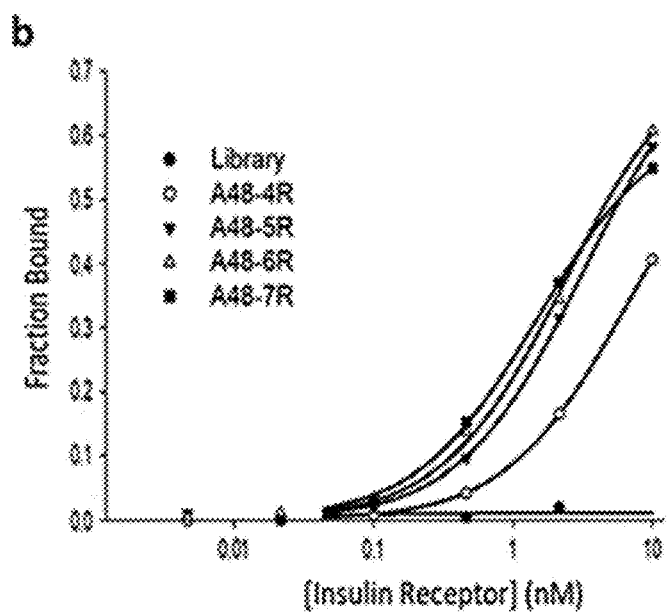
FIG. 2B
| | Library | A48-4R | A48-5R | A48-6R | A48-7R |
|---|---|---|---|---|---|
| Kd (nM) | 0.02 | 6.73 | 3.10 | 2.37 | 1.50 |
| Std. Errors | 8.E-02 | 2.E-01 | 1.E-01 | 2.E-01 | 8.E-02 |
| Bmax | 0.01 | 0.68 | 0.77 | 0.75 | 0.63 |
| Std. Errors | 7.E-03 | 8.E-03 | 1.E-02 | 2.E-02 | 1.E-02 |
FIG. 2C

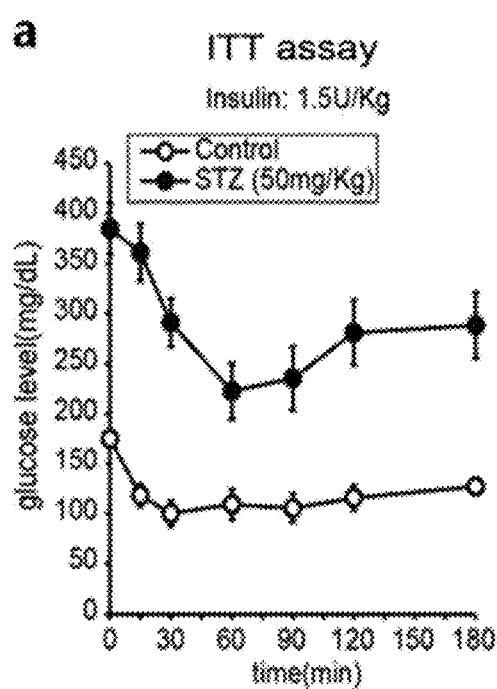
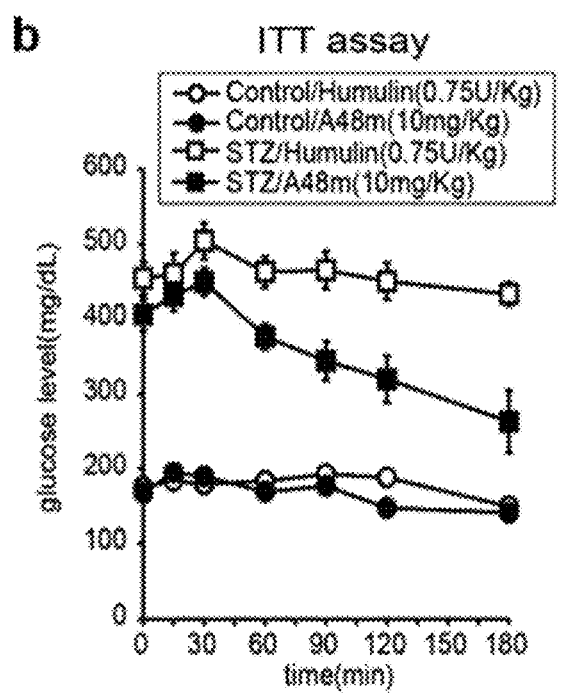
FIG. 5A
FIG. 5B

- Insulin 50nM for 5min
- A48m combi 3 200nM for 1h
- Insulin + A48ms for 5min
- Krebs HEPES buffer
- Fully differentiated 3T3-L1 adipocyte

```
                              SEQUENCE LISTING

<160> NUMBER OF SEQ ID NOS: 26

<210> SEQ ID NO 1
<211> LENGTH: 33
<212> TYPE: DNA
<213> ORGANISM: Artificial Sequence
<220> FEATURE:
<223> OTHER INFORMATION: A48
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(11)
<223> OTHER INFORMATION: naphtyl-uracil
<220> FEATURE:
<221> NAME/KEY: misc_feature
<222> LOCATION: (21)..(21)
<223> OTHER INFORMATION: naphtyl-uracil
<220> FEATURE:
<221> NAME/KEY: misc_feature
<222> LOCATION: (23)..(23)
<223> OTHER INFORMATION: naphtyl-uracil
<220> FEATURE:
<221> NAME/KEY: misc_feature
<222> LOCATION: (27)..(27)
<223> OTHER INFORMATION: naphtyl-uracil

<400> SEQUENCE: 1
cgcctggngn naagacaacc ncnaggncag gcg                                      33

<210> SEQ ID NO 2
<211> LENGTH: 17
<212> TYPE: DNA
<213> ORGANISM: Artificial Sequence
<220> FEATURE:
<223> OTHER INFORMATION: Insulin Aptamer primer_F

<400> SEQUENCE: 2
gagtgaccgt ccgcctg                                                        17

<210> SEQ ID NO 3
<211> LENGTH: 17
<212> TYPE: DNA
<213> ORGANISM: Artificial Sequence
<220> FEATURE:
<223> OTHER INFORMATION: Insulin Aptamer primer_R

<400> SEQUENCE: 3
ggctggtggt gtggctg                                                        17

<210> SEQ ID NO 4
<211> LENGTH: 32
<212> TYPE: DNA
<213> ORGANISM: Artificial Sequence
<220> FEATURE:
<223> OTHER INFORMATION: A48 seq 1-3
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(11)
<223> OTHER INFORMATION: naphtyl-uracil
```

-continued

<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(28)
<223> OTHER INFORMATION: naphtyl-uracil

<400> SEQUENCE: 4
cgcctggngn ncnaaacgac cncnaggnaa gg                                32

<210> SEQ ID NO 5
<211> LENGTH: 33
<212> TYPE: DNA
<213> ORGANISM: Artificial Sequence
<220> FEATURE:
<223> OTHER INFORMATION: A48 seq 1-4
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(11)
<223> OTHER INFORMATION: naphtyl-uracil
<220> FEATURE:
<221> NAME/KEY: misc_feature
<222> LOCATION: (21)..(21)
<223> OTHER INFORMATION: naphtyl-uracil
<220> FEATURE:
<221> NAME/KEY: misc_feature
<222> LOCATION: (23)..(23)
<223> OTHER INFORMATION: naphtyl-uracil
<220> FEATURE:
<221> NAME/KEY: misc_feature
<222> LOCATION: (27)..(27)
<223> OTHER INFORMATION: naphtyl-uracil

<400> SEQUENCE: 5
cgcctggngn naagacaacc ncnaggnaag gct                               33

<210> SEQ ID NO 6
<211> LENGTH: 33
<212> TYPE: DNA
<213> ORGANISM: Artificial Sequence
<220> FEATURE:
<223> OTHER INFORMATION: A48 seq 1-19(A48m)
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(11)
<223> OTHER INFORMATION: naphtyl-uracil
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)

```
<223> OTHER INFORMATION: naphtyl-uracil
<220> FEATURE:
<221> NAME/KEY: misc_feature
<222> LOCATION: (28)..(29)
<223> OTHER INFORMATION: naphtyl-uracil

<400> SEQUENCE: 6
cgcctggngn ncnagacgac cnanaggnna ggc                          33

<210> SEQ ID NO 7
<211> LENGTH: 33
<212> TYPE: RNA
<213> ORGANISM: Artificial Sequence
<220> FEATURE:
<223> OTHER INFORMATION: A48m combi 2
<220> FEATURE:
<221> NAME/KEY: misc_feature
<222> LOCATION: (1)..(2)
<223> OTHER INFORMATION: absent
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(10)
<223> OTHER INFORMATION: benzyl-uracil
<220> FEATURE:
<221> NAME/KEY: misc_feature
<222> LOCATION: (11)..(11)
<223> OTHER INFORMATION: naphtyl-uracil
<220> FEATURE:
<221> NAME/KEY: misc_feature
<222> LOCATION: (12)..(12)
<223> OTHER INFORMATION: absent
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (16)..(17)
<223> OTHER INFORMATION: absent
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(28)
<223> OTHER INFORMATION: benzyl-uracil
<220> FEATURE:
<221> NAME/KEY: misc_feature
<222> LOCATION: (29)..(29)
<223> OTHER INFORMATION: naphtyl-uracil
<220> FEATURE:
<221> NAME/KEY: misc_feature
<222> LOCATION: (33)..(33)
<223> OTHER INFORMATION: absent

<400> SEQUENCE: 7
nnccuggngn nnnagnngac cnanaggnna ggn                          33

<210> SEQ ID NO 8
<211> LENGTH: 33
<212> TYPE: RNA
<213> ORGANISM: Artificial Sequence
<220> FEATURE:
<223> OTHER INFORMATION: A48m combi 3
<220> FEATURE:
<221> NAME/KEY: misc_feature
```

```
<222> LOCATION: (1)..(2)
<223> OTHER INFORMATION: absent
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(10)
<223> OTHER INFORMATION: benzyl-uracil
<220> FEATURE:
<221> NAME/KEY: misc_feature
<222> LOCATION: (11)..(11)
<223> OTHER INFORMATION: naphtyl-uracil
<220> FEATURE:
<221> NAME/KEY: misc_feature
<222> LOCATION: (12)..(12)
<223> OTHER INFORMATION: absent
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(29)
<223> OTHER INFORMATION: naphtyl-uracil
<220> FEATURE:
<221> NAME/KEY: misc_feature
<222> LOCATION: (33)..(33)
<223> OTHER INFORMATION: absent

<400> SEQUENCE: 8
nnccuggngn nnnagacgac cnanaggnna ggn                                    33

<210> SEQ ID NO 9
<211> LENGTH: 33
<212> TYPE: RNA
<213> ORGANISM: Artificial Sequence
<220> FEATURE:
<223> OTHER INFORMATION: A48m combi 4
<220> FEATURE:
<221> NAME/KEY: misc_feature
<222> LOCATION: (1)..(2)
<223> OTHER INFORMATION: absent
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(10)
<223> OTHER INFORMATION: benzyl-uracil
<220> FEATURE:
<221> NAME/KEY: misc_feature
<222> LOCATION: (11)..(11)
<223> OTHER INFORMATION: naphtyl-uracil
<220> FEATURE:
<221> NAME/KEY: misc_feature
<222> LOCATION: (12)..(12)
<223> OTHER INFORMATION: absent
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (19)..(19)
<223> OTHER INFORMATION: absent
<220> FEATURE:
```

-continued

```
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(29)
<223> OTHER INFORMATION: naphtyl-uracil
<220> FEATURE:
<221> NAME/KEY: misc_feature
<222> LOCATION: (33)..(33)
<223> OTHER INFORMATION: absent

<400> SEQUENCE: 9
nnccuggngn nnnagacgnc cnanaggnna ggn                                   33

<210> SEQ ID NO 10
<211> LENGTH: 33
<212> TYPE: RNA
<213> ORGANISM: Artificial Sequence
<220> FEATURE:
<223> OTHER INFORMATION: A48m combi 5
<220> FEATURE:
<221> NAME/KEY: misc_feature
<222> LOCATION: (1)..(2)
<223> OTHER INFORMATION: absent
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(10)
<223> OTHER INFORMATION: benzyl-uracil
<220> FEATURE:
<221> NAME/KEY: misc_feature
<222> LOCATION: (11)..(11)
<223> OTHER INFORMATION: naphtyl-uracil
<220> FEATURE:
<221> NAME/KEY: misc_feature
<222> LOCATION: (12)..(12)
<223> OTHER INFORMATION: absent
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (16)..(17)
<223> OTHER INFORMATION: absent
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(29)
<223> OTHER INFORMATION: naphtyl-uracil
<220> FEATURE:
<221> NAME/KEY: misc_feature
<222> LOCATION: (33)..(33)
<223> OTHER INFORMATION: absent

<400> SEQUENCE: 10
nnccuggngn nnnagnngac cnanaggnna ggn                                   33

<210> SEQ ID NO 11
<211> LENGTH: 33
```

```
<212> TYPE: DNA
<213> ORGANISM: Artificial Sequence
<220> FEATURE:
<223> OTHER INFORMATION: general-formula 1
<220> FEATURE:
<221> NAME/KEY: misc_feature
<222> LOCATION: (1)..(1)
<223> OTHER INFORMATION: cytosine or absent
<220> FEATURE:
<221> NAME/KEY: misc_feature
<222> LOCATION: (2)..(2)
<223> OTHER INFORMATION: guanine or absent
<220> FEATURE:
<221> NAME/KEY: misc_feature
<222> LOCATION: (5)..(5)
<223> OTHER INFORMATION: thymine or uracil
<220> FEATURE:
<221> NAME/KEY: misc_feature
<222> LOCATION: (8)..(8)
<223> OTHER INFORMATION: naphtyl-uracil
<220> FEATURE:
<221> NAME/KEY: misc_feature
<222> LOCATION: (10)..(10)
<223> OTHER INFORMATION: naphtyl-uracil or benzyl-uracil
<220> FEATURE:
<221> NAME/KEY: misc_feature
<222> LOCATION: (11)..(11)
<223> OTHER INFORMATION: naphtyl-uracil
<220> FEATURE:
<221> NAME/KEY: misc_feature
<222> LOCATION: (12)..(12)
<223> OTHER INFORMATION: cytosine or absent
<220> FEATURE:
<221> NAME/KEY: misc_feature
<222> LOCATION: (13)..(13)
<223> OTHER INFORMATION: naphtyl-uracil
<220> FEATURE:
<221> NAME/KEY: misc_feature
<222> LOCATION: (15)..(15)
<223> OTHER INFORMATION: guanine or adenine
<220> FEATURE:
<221> NAME/KEY: misc_feature
<222> LOCATION: (16)..(16)
<223> OTHER INFORMATION: adenine or absent
<220> FEATURE:
<221> NAME/KEY: misc_feature
<222> LOCATION: (17)..(17)
<223> OTHER INFORMATION: cytosine or absent
<220> FEATURE:
<221> NAME/KEY: misc_feature
<222> LOCATION: (22)..(22)
<223> OTHER INFORMATION: naphtyl-uracil
<220> FEATURE:
<221> NAME/KEY: misc_feature
<222> LOCATION: (23)..(23)
<223> OTHER INFORMATION: cytosine or adenine
<220> FEATURE:
<221> NAME/KEY: misc_feature
<222> LOCATION: (24)..(24)
<223> OTHER INFORMATION: naphtyl-uracil
<220> FEATURE:
<221> NAME/KEY: misc_feature
<222> LOCATION: (28)..(28)
<223> OTHER INFORMATION: naphtyl-uracil or benzyl-uracil
<220> FEATURE:
<221> NAME/KEY: misc_feature
<222> LOCATION: (29)..(29)
<223> OTHER INFORMATION: adenine or naphtyl-uracil
<220> FEATURE:
<221> NAME/KEY: misc_feature
<222> LOCATION: (33)..(33)
<223> OTHER INFORMATION: cytosine or absent

<400> SEQUENCE: 11
nnccnggngn nnnannngac cnnnaggnna ggn                           33

<210> SEQ ID NO 12
```

```
<211> LENGTH: 34
<212> TYPE: DNA
<213> ORGANISM: Artificial Sequence
<220> FEATURE:
<223> OTHER INFORMATION: Generic sequence library motif
<220> FEATURE:
<221> NAME/KEY: misc_feature
<222> LOCATION: (7)..(18)
<223> OTHER INFORMATION: Random deoxyribonucleotide
<220> FEATURE:
<221> NAME/KEY: misc_feature
<222> LOCATION: (22)..(25)
<223> OTHER INFORMATION: Random deoxyribonucleotide
<220> FEATURE:
<221> NAME/KEY: misc_feature
<222> LOCATION: (28)..(28)
<223> OTHER INFORMATION: deoxyribonucleotide

<400> SEQUENCE: 12
cgcctgnnnn nnnnnnnnac cnnnnggnca ggcg                                    34

<210> SEQ ID NO 13
<211> LENGTH: 33
<212> TYPE: DNA
<213> ORGANISM: Artificial Sequence
<220> FEATURE:
<223> OTHER INFORMATION: Library 33 mer
<220> FEATURE:
<221> NAME/KEY: misc_feature
<222> LOCATION: (7)..(7)
<223> OTHER INFORMATION: Random deoxyribonucleotide
<220> FEATURE:
<221> NAME/KEY: misc_feature
<222> LOCATION: (8)..(8)
<223> OTHER INFORMATION: Napthyl-uracil
<220> FEATURE:
<221> NAME/KEY: misc_feature
<222> LOCATION: (10)..(11)
<223> OTHER INFORMATION: Napthyl-uracil
<220> FEATURE:
<221> NAME/KEY: misc_feature
<222> LOCATION: (12)..(15)
<223> OTHER INFORMATION: Random deoxyribonucleotide
<220> FEATURE:
<221> NAME/KEY: misc_feature
<222> LOCATION: (17)..(17)
<223> OTHER INFORMATION: Random deoxyribonucleotide
<220> FEATURE:
<221> NAME/KEY: misc_feature
<222> LOCATION: (21)..(21)
<223> OTHER INFORMATION: Napthyl-uracil
<220> FEATURE:
<221> NAME/KEY: misc_feature
<222> LOCATION: (22)..(22)
<223> OTHER INFORMATION: Random deoxyribonucleotide
<220> FEATURE:
<221> NAME/KEY: misc_feature
<222> LOCATION: (23)..(23)
<223> OTHER INFORMATION: Napthyl-uracil
<220> FEATURE:
<221> NAME/KEY: misc_feature
<222> LOCATION: (27)..(27)
<223> OTHER INFORMATION: Napthyl-uracil
<220> FEATURE:
<221> NAME/KEY: misc_feature
<222> LOCATION: (28)..(28)
<223> OTHER INFORMATION: Random deoxyribonucleotide

<400> SEQUENCE: 13
cgcctgnngn nnnnncnacc nnnaggnnag gcg                                     33

<210> SEQ ID NO 14
<211> LENGTH: 33
<212> TYPE: DNA
<213> ORGANISM: Artificial Sequence
```

```
<220> FEATURE:
<223> OTHER INFORMATION: Candidate Library Sequence A48on

<400> SEQUENCE: 14
cgcctggtgt taagacaacc tctaggtcag gcg                                33

<210> SEQ ID NO 15
<211> LENGTH: 33
<212> TYPE: DNA
<213> ORGANISM: Artificial sequence
<220> FEATURE:
<223> OTHER INFORMATION: Candidate Library Sequence seq 1-1

<400> SEQUENCE: 15
cgcctgcatt acgcatgagt gtagatccgt cag                                33

<210> SEQ ID NO 16
<211> LENGTH: 33
<212> TYPE: DNA
<213> ORGANISM: Artificial Sequence
<220> FEATURE:
<223> OTHER INFORMATION: Candidate Library Sequence 1-2

<400> SEQUENCE: 16
cgcctgcatt acgcatgagt ctagatccgt cag                                33

<210> SEQ ID NO 17
<211> LENGTH: 32
<212> TYPE: DNA
<213> ORGANISM: Artificial Sequence
<220> FEATURE:
<223> OTHER INFORMATION: Candidate Library Sequence seq1-3

<400> SEQUENCE: 17
cgcctggtgt tctaaacgac ctctaggtaa gg                                 32

<210> SEQ ID NO 18
<211> LENGTH: 33
<212> TYPE: DNA
<213> ORGANISM: Artificial Sequence
<220> FEATURE:
<223> OTHER INFORMATION: Candidate Library Sequence seq1-4

<400> SEQUENCE: 18
cgcctggtgt taagacaacc tctaggtaag gct                                33

<210> SEQ ID NO 19
<211> LENGTH: 30
<212> TYPE: DNA
<213> ORGANISM: Artificial Sequence
<220> FEATURE:
<223> OTHER INFORMATION: Candidate Library Sequence seq1-5

<400> SEQUENCE: 19
cgcctgcatt acgcatgagt ctagatccgt                                    30

<210> SEQ ID NO 20
<211> LENGTH: 33
<212> TYPE: DNA
<213> ORGANISM: Artificial Sequence
<220> FEATURE:
<223> OTHER INFORMATION: Candidate Library Sequence seq1-6

<400> SEQUENCE: 20
cgcctgaatt acgcatgagt gtagatccgt cag                                33
```

```
<210> SEQ ID NO 21
<211> LENGTH: 33
<212> TYPE: DNA
<213> ORGANISM: Artificial Sequence
<220> FEATURE:
<223> OTHER INFORMATION: Candidate Library Sequence seq1-7

<400> SEQUENCE: 21
cgcctggtgt taagtctacc tctaggttag gct                              33

<210> SEQ ID NO 22
<211> LENGTH: 32
<212> TYPE: DNA
<213> ORGANISM: Artificial Sequence
<220> FEATURE:
<223> OTHER INFORMATION: Candidate Library Sequence seq1-8

<400> SEQUENCE: 22
cgcctggtgt taagacaacc tctaggtaag gc                               32

<210> SEQ ID NO 23
<211> LENGTH: 33
<212> TYPE: DNA
<213> ORGANISM: Artificial Sequence
<220> FEATURE:
<223> OTHER INFORMATION: Candidate Library Sequence seq1-9

<400> SEQUENCE: 23
cgcctgcatt acgcatgagt gtagatccgt cgg                              33

<210> SEQ ID NO 24
<211> LENGTH: 32
<212> TYPE: DNA
<213> ORGANISM: Artificial Sequence
<220> FEATURE:
<223> OTHER INFORMATION: Candidate Library Sequence seq1-10

<400> SEQUENCE: 24
cgcctggtgt taagtctacc tctaggttag gc                               32

<210> SEQ ID NO 25
<211> LENGTH: 30
<212> TYPE: DNA
<213> ORGANISM: Artificial Sequence
<220> FEATURE:
<223> OTHER INFORMATION: Candidate Library Sequence seq 1-11

<400> SEQUENCE: 25
cgcctgcatt acgcatgagt gtagatccgt                                  30

<210> SEQ ID NO 26
<211> LENGTH: 33
<212> TYPE: DNA
<213> ORGANISM: Artificial Sequence
<220> FEATURE:
<223> OTHER INFORMATION: Candidate Library Sequence seq1-19

<400> SEQUENCE: 26
cgcctggtgt tctagacgac ctataggtta ggc                              33
```

INSULIN RECEPTOR APTAMER AND PHARMACEUTICAL COMPOSITION FOR TREATING DIABETES COMPRISING THE SAME

CROSS REFERENCE TO RELATED APPLICATIONS

This application is a U.S. National Phase Application filed under 35 U.S.C. § 371 and claims priority to International Application No. PCT/KR2018/005400, filed May 10, 2018, the disclosure of which is incorporated herein by reference.

TECHNICAL FIELD

The present invention relates to a DNA aptamer specifically binding to an insulin receptor, a pharmaceutical composition for treating diabetes including the same, and a composition for diagnosing diabetes including the DNA aptamer.

BACKGROUND ART

Insulin, as a hormone regulating a blood sugar level and secreted by the pancreatic islets in the human body, plays a role in supplying energy to cells by transferring excess glucose from blood into the cells and maintaining a normal blood sugar level. However, in patients with diabetes, insulin cannot perform normal functions thereof due to lack of insulin, insulin resistance, and loss of function of beta cells. Thus, patients with diabetes cannot use glucose in the blood as an energy source and have symptoms of high blood sugar levels excreting glucose in the urine, causing various complications. Therefore, patients with diabetes caused by the failure to produce insulin (Type I) or by insulin resistance (Type II) need to be treated with medications containing insulin, and the blood sugar levels of the patients may be maintained within normal ranges by administration of insulin.

Thus, although various types of insulin derivatives have recently been developed to regulate blood sugar levels of patients with diabetes within normal ranges, insulin induces cell division in addition to glucose uptake and modification of an amino acid sequence introduced into several insulin derivatives enhances binding affinity for insulin-like growth factor-1 (IGF-1) receptor and activation thereof. Concerns about side effects caused by prolonged administration of insulin for the treatment of diabetes such as an increase in incidence of cancer and atherosclerosis have been continuously raised. Several epidemiological studies have also reported a significant correlation between prolonged administration of insulin and increased cancer rates. Thus, development of an insulin receptor-biased agonist capable of only increasing glucose uptake without inducing cell division will be an alternative to administration of insulin.

Aptamer is a single-stranded nucleotide chain such as DNA and RNA having a stable three-dimensional structure and specifically binding to a target molecule with a high affinity. Since 1990, many aptamers capable of binding to various target molecules such as low molecular weight organic materials, peptides, and membrane proteins have been discovered. Due to high binding affinity and the ability to selectively bind to a target molecule, aptamers have been used for differentiating specific substances.

Currently, most of the efforts to develop functional aptamers using high binding affinity and specificity have focused on the ability of the aptamers to inhibit a target. Particularly, various types of inhibitory aptamers that inhibit the activity of a target molecule have been developed to treat diseases for clinical applications (e.g., Macugen, Fovista). However, considering that interactions between molecules inevitably involve structural changes, activation of protein function is expected in the case where aptamer-protein binding induces an appropriate structural change of protein. Thus, theoretically, aptamers have potential to serve as functional agonists by mimicking a specific protein-protein binding. However, development of agonist aptamers capable of activating functions of targets still remains a difficult problem.

DISCLOSURE

Technical Problem

The present inventors have made intensive efforts to develop therapeutic agents for diabetes with reduced side effects and have found an aptamer that activates only signaling related to glucose uptake by inducing selective phosphorylation of the insulin receptor and a pharmaceutical composition for treating of diabetes including the same, thereby completing the present invention.

Technical Solution

An object of the present invention is to provide an insulin receptor aptamer having a nucleotide sequence of General Formula 1 below.

5'-R1-R2-C-C-R3-G-G-P-G-R4-P-R5-P-A-R6-R7-R8-G-A-C-C-P-R9-P-A-G-G-R10-R11-A-G-G-R12-3'  General Formula 1 (SEQ ID NO:11)

In General Formula 1 (SEQ ID NO:11) above,

R1 is a cytosine nucleotide (C) or absent;
R2 is a guanine nucleotide (G) or absent;
R3 is a thymine nucleotide (T) or a uracil nucleotide (U);
R4 is a naphthyl-uracil nucleotide (P) or a benzyl-uracil nucleotide (Z);
R5 is a cytosine nucleotide (C) or absent;
R6 is a guanine nucleotide (G) or an adenine nucleotide (A);
R7 is an adenine nucleotide (A) or absent;
R8 is a cytosine nucleotide (C) or absent;
R9 is a cytosine nucleotide (C) or an adenine nucleotide (A);
R10 is a naphthyl-uracil nucleotide (P) or a benzyl-uracil nucleotide (Z);
R11 is an adenine nucleotide (A) or a naphthyl-uracil nucleotide (P); and
R12 is a cytosine nucleotide (C) or absent, wherein the term 'absent' indicates a site from which the nucleotide is removed or a linker.

Another object of the present invention is to provide an insulin receptor agonist including the insulin receptor aptamer.

Another object of the present invention is to provide a pharmaceutical composition for preventing or treating an insulin-related disease including the insulin receptor aptamer as an active ingredient.

Another object of the present invention is to provide a method of preventing or treating an insulin-related disease, the method including administering the pharmaceutical composition to a subject except a human.

Another object of the present invention is to provide a composition for diagnosing diabetes or diabetic complications including the insulin receptor aptamer as an active ingredient.

Advantageous Effects

Since the insulin receptor aptamer according to the present invention exhibits a higher degree of activating a downstream signaling pathway of an insulin receptor than insulin or existing insulin receptor aptamers conventionally used for treatment of insulin-related diseases such as diabetes, the insulin receptor aptamer according to the present invention may be effectively used in compositions for preventing or treating insulin-related diseases.

DESCRIPTION OF DRAWINGS

FIG. 2A-C illustrates binding affinity test results of pools of respective rounds by RI labeling.

FIG. 5A-B shows ITT assay results of A48m aptamer, insulin, and Humulin.

BEST MODE

Figure 1A:
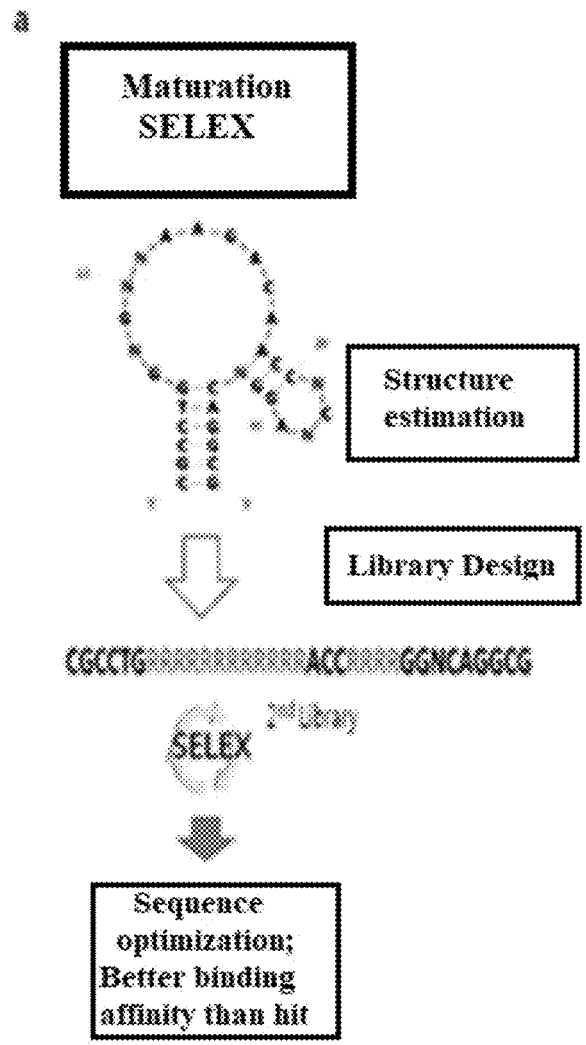
FIG. 1a is a schematic diagram illustrating an aptamer SELEX process (SEQ ID NO:12)

Hereinafter, the present invention will be described in detail. Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

An aspect of the present invention to achieve the objects of the present invention provides an insulin receptor aptamer having a nucleotide sequence represented by General Formula 1 below.

5'-R1-R2-C-C-R3-G-G-P-G-R4-P-R5-P-A-R6-R7-R8-G-A-C-C-P-R9-P-A-G-G-R10-R11-A-G-G-R12-3'   General Formula 1 (SEQ ID NO:11)

In General Formula 1 (SEQ ID NO:11) above,
R1 is a cytosine nucleotide (C) or absent;
R2 is a guanine nucleotide (G) or absent;
R3 is a thymine nucleotide (T) or a uracil nucleotide (U);
R4 is a naphthyl-uracil nucleotide (P) or a benzyl-uracil nucleotide (Z);
R5 is a cytosine nucleotide (C) or absent;
R6 is a guanine nucleotide (G) or an adenine nucleotide (A);
R7 is an adenine nucleotide (A) or absent;
R8 is a cytosine nucleotide (C) or absent;
R9 is a cytosine nucleotide (C) or an adenine nucleotide (A);
R10 is a naphthyl-uracil nucleotide (P) or a benzyl-uracil nucleotide (Z);
R11 is an adenine nucleotide (A) or a naphthyl-uracil nucleotide (P); and
R12 is a cytosine nucleotide (C) or absent,
wherein the term 'absent' indicates a site from which the nucleotide is removed or a linker.

As used herein, the term "insulin receptor aptamer" refers to an aptamer capable of binding to insulin with specific affinity. The insulin receptor may be derived from human insulin receptor protein, but is not limited thereto. Also, the "aptamer" is a short single-stranded oligonucleotide capable of specifically recognizing a target substance with a high affinity and may form a three-dimensional structure capable of specifically binding to the target substance with a high affinity. Also, the aptamer, which may not only specifically bind to a target protein, but also efficiently inhibit a function thereof in most cases, may be used to determine the function of a target protein.

The insulin receptor aptamer is characterized by specifically binding to the insulin receptor and may consist of 25 to 90 of nucleotides, particularly 27 to 80 nucleotides, more particularly 27 to 50 nucleotides, without being limited thereto.

The present inventors have conducted research to develop an insulin receptor aptamer having improved binding affinity for an insulin receptor, phosphorylation activity, and serum stability based on the insulin receptor aptamer (A48, SEQ ID NO: 1) disclosed in Korean Patent Publication No. 10-2017-0013178.

Accordingly, the present inventors have found that binding affinity for the insulin receptor, phosphorylation activity, and serum stability of insulin receptor aptamers are improved by sequence optimization and chemical modification, for example, by substituting one base of a particular site of the nucleotide sequence with another type of base; removing a base from a particular site and modifying a pentose site to a linker or spacer; or causing additional chemical modification in a nucleotide, thereby completing the present invention.

According to the present invention, based on the A48 aptamer, it was confirmed that the binding affinity for the insulin receptor is improved (Example 1-7) when a $12^{th}$ nucleotide of the nucleotide sequence is substituted with a cytosine nucleotide (C), a $17^{th}$ nucleotide is substituted with a guanine nucleotide (G), a $22^{nd}$ nucleotide is substituted with an adenine nucleotide (A), a $28^{th}$ nucleotide is substituted with a naphthyl-uracil nucleotide (P), a $33^{rd}$ nucleotide is removed, and a naphthyl-uracil nucleotide (P) is added between $12^{nd}$ and $13^{th}$ nucleotides, thereby deducing a novel sequence of an insulin receptor aptamer (A48m, SEQ ID NO: 6). It was also confirmed that phosphorylation activity and serum stability of the insulin receptor are improved when $1^{st}$, $2^{nd}$, $12^{nd}$, and $33^{rd}$ nucleotides of the nucleotide sequence of the A48m aptamer are substituted with a linker or a spacer, and a $10^{th}$ nucleotide thereof is substituted with a benzyl-uracil nucleotide (Z). Additionally, it was confirmed that phosphorylation activity and serum stability of the insulin receptor are improved when 16$^{th}$ and 17$^{th}$ nucleotides are selectively substituted with a linker or a spacer, and a 28$^{th}$ nucleotide thereof was substituted with a benzyl-uracil nucleotide (Z). Also, it was confirmed that phosphorylation activity and serum stability of the insulin receptor are improved by removing the 1st 2$^{nd}$, and 33$^{rd}$ nucleotides (Examples 3-1 and 3-2).

The effect of the insulin receptor aptamer may further be improved by chemical modification of adding a methoxy group to at least one of 3$^{rd}$, 4$^{th}$, 5$^{th}$, 14$^{th}$, 16$^{th}$, 19$^{th}$, 21$^{st}$, 23$^{rd}$, 27$^{th}$, 30$^{th}$, 31$^{st}$, and 32$^{nd}$ nucleotides or adding a fluoro group to at least one of 17$^{th}$ and 20$^{th}$ nucleotides of the nucleotide sequence of the modified aptamer.

The insulin receptor aptamer according to the present invention includes a nucleotide sequence represented by General Formula 1 above. General Formula 1 above may be expressed as SEQ ID NO: 11. General Formula 1 above may include an adenine nucleotide (A), a thymine nucleotide (T), a guanine nucleotide (G), a cytosine nucleotide (C), an uracil nucleotides (U), and a nucleotide including a modified uracil substituted with a hydrophobic functional group at position 5. The hydrophobic functional group may include a naphthyl group, a benzyl group, a pyrrolebenzyl group, an isobutyl group, or tryptophan, particularly a naphthyl group or a benzyl group according to an embodiment, but is not limited thereto. Uracil modified by substitution with a naphthyl group is referred to as naphthyl-uracil and denoted by P in General Formula 1 above. Also, uracil modified by substitution with a benzyl is referred to as benzyl-uracil and denoted by Z in General Formula 1 above.

The naphthyl group is represented by Formula 1 below, and the benzyl group is represented by Formula 2 below.

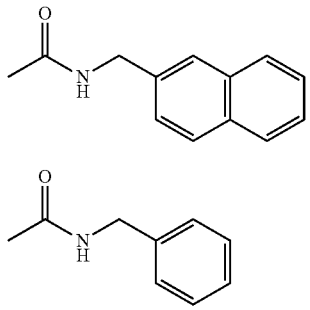

[Formula 1]

[Formula 2]

In addition, the insulin receptor aptamer according to the present invention may be an aptamer having a nucleotide sequence of General Formula 1 above, one or more nucleotides of which are absent.

The "absent" may mean that a nucleotide is removed or a linker. Particularly, a removal of a nucleotide may refer to a removal of a base or a pentose of the nucleotide, and further refer to a removal of the entire nucleotide including a phosphate backbone as well as the base and the pentose. In addition, particularly, the linker may refer to a nucleotide substituted with a linker including a phosphate backbone alone with an empty space although a base of the nucleotide or a nucleoside including the base and a pentose is removed, or may refer to a state connected to adjacent nucleotides at both sides of the empty space with an intrinsic distance maintained, but is not limited thereto.

The term linker as used herein may be used interchangeably with the term 'spacer'. The linker or spacer may consist of 3 carbon atoms, but is not limited thereto as long as a constant distance may be maintained between the nucleotides. Particularly, the linker or spacer according to the present invention may a linker or spacer consisting of 3 carbon atoms and may be referred to as a C3 linker or C3 spacer. The C3 linker or spacer may be included at the 5'-end, at the 3'-end, in the middle, or at both ends, particularly, in the middle, of the insulin receptor aptamer according to the present invention, but is not limited thereto. Structures in which the C3 linker is linked to the 5'-end (Formula 3), the 3'-end (Formula 4), and the middle (Formula 5) of a nucleotide sequence are shown in the following formulae.

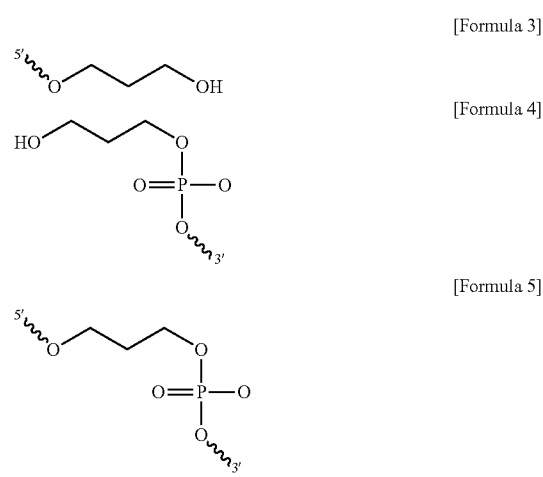

[Formula 3]

[Formula 4]

[Formula 5]

Particularly, at least one of R1, R2, R5, R7, R8, and R12 of General Formula 1 above may be a C3-linker, at least one of R1, R2, and R12 may be a position from which the nucleotide is removed, and at least one of R5, R7, and R8 may be a C3-linker, without being limited thereto.

The insulin receptor aptamer according to the present invention may be: an aptamer having a nucleotide sequence represented by General Formula 1 above wherein the 12$^{th}$ nucleotide is a cytosine nucleotide (C) and a 18$^{th}$ nucleotide is a guanine nucleotide (G); an aptamer having a nucleotide sequence represented by General Formula 1 above wherein the 12$^{th}$ nucleotide is a cytosine nucleotide (C), a 15$^{th}$ nucleotide is an adenine nucleotide (A), the 18$^{th}$ nucleotide is a guanine nucleotide (G), a 29$^{th}$ nucleotide is an adenine nucleotide (A), and the 33$^{rd}$ nucleotide is removed; or an aptamer having a nucleotide sequence represented by General Formula 1 above wherein the 12$^{th}$ nucleotide is a cytosine nucleotide (C), the 18$^{th}$ nucleotide is a guanine nucleotide (G), the 23$^{rd}$ nucleotide is an adenine nucleotide (A) and the 29$^{th}$ nucleotide is a naphthyl-uracil nucleotide (P), but is not limited thereto. The aptamers may be aptamers having improved binding affinity for the insulin receptor when compared with the conventional A48 aptamer, particularly, may be referred to as A48m aptamer or A48 seq 1-19 aptamer.

The insulin receptor aptamer according to the present invention may be an aptamer having a nucleotide sequence represented by General Formula 1 above, wherein R6 is a guanine nucleotide (G), R9 is an adenine nucleotide (A), R11 is a naphthyl-uracil nucleotide (P), and R12 is a cytosine nucleotide (C), particularly, the A48m aptamer, but is not limited thereto. The aptamer including the nucleotide sequence as described above may have better binding affinity for the insulin receptor than that of the conventional A48 aptamer or may have better binding affinity for the insulin receptor than that of A48 seq 1-3 or A48 seq 1-4 aptamer.

The insulin receptor aptamer according to the present invention may be an aptamer represented by General Formula 1 above having a nucleotide sequence, wherein at least one of R1, R2, R5, R7, R8, and R12 is absent, particularly, a nucleotide sequence wherein all of the R1, R2, R5 and R12 are absent, or a nucleotide sequence wherein the nucleotides of R1, R2, and R12 are removed, but is not limited thereto. The aptamers may have higher insulin receptor phosphorylation activity, particularly, phosphorylation activity of Y1150 of the insulin receptor, than the A48m aptamer. Also, the aptamers may be referred to as A48m combi 2, 3, 4, or 5, without being limited thereto.

In addition, the insulin receptor aptamer according to the present invention may be an aptamer having a nucleotide sequence in which at least one of R7 and R8 of General Formula 1 above is absent, particularly, both R7 and R8 are absent; R7 is an adenine nucleotide (A) and R8 is a cytosine nucleotide (C); or R7 is absent and R8 is a cytosine nucleotide (C), without being limited thereto.

The insulin receptor aptamer according to the present invention may be an aptamer having a nucleotide sequence represented by General Formula 1 above in which R4 is a benzyl-uracil nucleotide (Z), and/or R10 is a naphthyl-uracil nucleotide (P). Specifically, the aptamer in which the R4 is a benzyl-uracil nucleotide (Z) may be an aptamer having higher insulin receptor phosphorylation activity, particularly, phosphorylation activity of Y1150 region of the insulin receptor, than the A48m aptamer, and may be an aptamer having improved stability in serum. Also, the aptamer may particularly be A48m combi 2, 3, 4, or 5, without being limited thereto.

Also, the aptamer may be an aptamer having a nucleotide sequence represented by General Formula 1 above, wherein R3 is a thymine nucleotide (T) or an uracil nucleotide (U). Thymine and uracil are bases distinguished from each other by merely the presence or absence of methyl group on the fifth carbon, and in general, thymine is found in DNA and uracil is found in RNA.

According to the present invention, since it was confirmed that the insulin receptor phosphorylation activities are similar when R3 of the aptamer of General Formula 1 above is a thymine nucleotide (T) or an uracil nucleotide (U) (Example 3-1), the thymine nucleotide (T) and the uracil nucleotide (U) may be mutually substitutable at R3 of the aptamer according to the present invention represented by General Formula 1 above.

Also, the aptamer wherein R10 is a naphthyl-uracil nucleotide (P) may be an aptamer higher insulin receptor phosphorylation activity and better serum stability than the A48m combi 2, and the aptamer may be, particularly, A48m combi 3, 4, or 5, without being limited thereto.

The aptamer may be an aptamer represented by General Formula 1 above wherein both R4 and R10 are a naphthyl-uracil nucleotide (P) or a benzyl-uracil nucleotide (Z); or an aptamer having a nucleotide sequence wherein R4 is a benzyl-uracil nucleotide (Z) and R10 is a naphthyl-uracil nucleotide (P).

The insulin receptor aptamer according to the present invention may be an aptamer having a nucleotide sequence of A48m (SEQ ID NO: 6), A48m combi 2 (SEQ ID NO: 7), A48m combi 3 (SEQ ID NO: 8), A48m combi 4 (SEQ ID NO: 9), or A48m combi 5 (SEQ ID NO: 10), but is not limited thereto.

The A48m aptamer may be an aptamer having a nucleotide sequence represented by General Formula 1 above wherein the $12^{th}$ nucleotide is a cytosine nucleotide (C), the $18^{th}$ nucleotide is a guanine nucleotide (G), the $23^{rd}$ nucleotide is an adenine nucleotide (A), and the $29^{th}$ nucleotide is a naphthyl-uracil nucleotide (P), particularly, an aptamer having a nucleotide sequence of SEQ ID NO: 6.

The A48m combi 2 aptamer may an aptamer having a nucleotide sequence represented by General Formula 1 above wherein the $1^{th}$ nucleotide is absent, the $2^{nd}$ nucleotide is absent, the $10^{th}$ nucleotide is a benzyl-uracil nucleotide (Z), the $12^{th}$ nucleotide is absent, the $16^{th}$ nucleotide is absent, the $17^{th}$ nucleotide is absent, the $28^{th}$ nucleotide is a benzyl-uracil nucleotide (Z), and the $33^{rd}$ nucleotide is absent, particularly, an aptamer having a nucleotide sequence of SEQ ID NO: 7.

The A48m combi 3 aptamer may be an aptamer having a nucleotide sequence represented by General Formula 1 above wherein the $1^{st}$ nucleotide is absent, the $2^{nd}$ nucleotide is absent, the $10^{th}$ nucleotide is a benzyl-uracil nucleotide (Z), the $12^{th}$ nucleotide is absent, and the $33^{rd}$ nucleotide is absent, particularly, an aptamer having a nucleotide sequence of SEQ ID NO: 8.

The A48m combi 4 aptamer may be an aptamer having a nucleotide sequence represented by General Formula 1 above wherein the $1^{th}$ nucleotide is absent, the $2^{nd}$ nucleotide is absent, the $10^{th}$ nucleotide is a benzyl-uracil nucleotide (Z), the $12^{th}$ nucleotide is absent, the $16^{th}$ nucleotide is absent, and the $33^{rd}$ nucleotide is absent, particularly, an aptamer having a nucleotide sequence of SEQ ID NO: 9.

The A48m combi 5 aptamer may be an aptamer having a nucleotide sequence represented by General Formula 1 above wherein the $1^{th}$ nucleotide is absent, the $2^{nd}$ nucleotide is absent, the $10^{th}$ nucleotide is a benzyl-uracil nucleotide (Z), the $12^{th}$ nucleotide is absent, the $16^{th}$ nucleotide is absent, the $17^{th}$ nucleotide is absent, and the $33^{rd}$ nucleotide is absent, particularly, an aptamer having a nucleotide sequence of SEQ ID NO: 10.

It was confirmed that the A48m, A48m combi 2, A48m combi 3, A48m combi 4 and A48m combi 5 aptamers have higher binding affinity for the insulin receptor (Example 1-7), higher insulin receptor phosphorylation activity (Example 3-1), and higher stability in serum (Example 3-2), than the conventional A48 aptamer, thereby exhibiting superior effects in vivo to the conventional insulin receptor aptamer.

At least one nucleotide of the insulin receptor aptamer according to the present invention may be modified at the 5'-end, the 3'-end, the middle, or both ends to improve stability in serum or adjust renal clearance by increasing resistance against a nucleotidase. Such a process of modifying the nucleotide is referred to as a post-SELEX process.

Modification of the post-SELEX process is performed by binding at least one selected from the group consisting of polyethylene glycol (PEG), biotin, inverted deoxythymidine (idT), locked nucleic acid (LNA), a methoxy group (—OMe), an amino group (—NH$_2$), a fluoro group (—F), an amine linker, a thiol linker, and cholesterol, particularly, a methoxy group or a fluoro group, to the 5'-end, the 3'-end, the middle, or both ends, but is not limited thereto.

As one example of the present invention, the methoxy group may be bound to position 2 of a pentose of at least one nucleotide selected from the $3^{rd}$, $4^{th}$, $5^{th}$, $14^{th}$, $16^{th}$, $19^{th}$, $21^{st}$, $23^{rd}$, $27^{th}$, $30^{th}$, $31^{st}$, and $32^{nd}$ nucleotides of General Formula 1 above, without being limited thereto.

As another example of the present invention, the fluoro group may be bound to position 2 of a pentose of at least one nucleotide selected from the $17^{th}$ and $20^{th}$ nucleotides of General Formula 1 above, without being limited thereto.

The insulin receptor aptamer according to the present invention may be an aptamer binding to an insulin receptor at a dissociation constant (Kd) of 0.1 nM to 5 nM, but is not limited thereto.

As used herein, the term "dissociation constant (Kd)" refers to a criterion for measuring the degree of binding between a membrane protein and a ligand. A lower Kd value indicates a better binding affinity. According to an embodiment of the present invention, it was confirmed that the dissociation constants between the insulin receptor and each of the A48 seq 1-3, A48 seq 1-4, and A48 seq 1-19 aptamers are lower than that a dissociation constant between the insulin receptor and the A48 aptamer that is a conventional insulin receptor aptamer (Example 1-7), indicating that the aptamer according to the present invention had a high binding affinity for the insulin receptor.

Also, the insulin receptors aptamer according to the present invention may phosphorylate Y1150 of the insulin receptor, but is not limited thereto. Particularly, since it was confirmed that the aptamer according to the present invention phosphorylates only Y1150 among 6 tyrosines (Y960, Y1146, Y1150, Y1151, Y1316, and Y1322) (Example 3-3), indicating that the aptamer may selectively activate the downstream signaling pathway of insulin.

Another aspect of the present invention to achieve the objects of the present invention provides an insulin receptor agonist including the insulin receptor aptamer. The insulin receptor aptamer is as described above.

As used herein, the term "agonist of insulin receptor" refers to a pharmaceutically acceptable preparation selectively binding to the insulin receptor. In general, the insulin receptor agonist means a new kind of therapeutic agent for diabetes developed to effectively regulate a blood sugar level. The insulin receptor agonist of the present invention has a property of specifically binding to the insulin receptor without side effects of cancer incidence. Therefore, the insulin receptor agonist may be used as a use for diagnosing or treating various diseases related to insulin.

Another aspect of the present invention to achieve the objects of the present invention provides a pharmaceutical composition for preventing or treating an insulin-related disease including the insulin receptor aptamer as an active ingredient. The insulin receptor aptamer is as described above.

As used herein, the term "insulin-related disease" refers to a disease associated with abnormal secretion of insulin, nonideal binding between insulin and the insulin receptor, or nonideal activation of the insulin receptor and a downstream signaling protein of the insulin receptor, and examples of the insulin-related disease may include diabetes, diabetic complications, metabolic syndrome, obesity, and cardiovascular diseases, but are not limited thereto.

As used herein, the term "prevention" or "preventing" means all actions that inhibit or delay the onset of an insulin-related disease by administering the composition according to the present invention to a subject. As used herein, the term "treatment" or "treating" means all actions intended to ameliorate or beneficially change a symptom associated with the insulin-related disease by administering the composition according to the present invention to a subject.

The pharmaceutical composition according to the present invention may further include a pharmaceutically acceptable carrier in addition to the insulin receptor aptamer included as an active ingredient.

As used herein, the term "pharmaceutically acceptable" refers to a property of a compound commonly used in the field of pharmaceuticals which does not cause significant irritation to an organism into which the compound is administered and does not damage the biological activity and physical properties of the compound.

The pharmaceutical composition according to the present invention may be formulated with the carrier to be used as foods, pharmaceuticals, feed additives, and beverage additives.

In the present invention, types of the carriers are not particularly limited, and any carrier commonly available in the art may be used. Examples of the carrier may include, but are not limited to, a saline solution, sterile water, a Ringer's solution, a buffer solution, an albumin injection solution, lactose, dextrose, sucrose, sorbitol, mannitol, xylitol, erythritol, maltitol, maltodextrin, glycerol, ethanol, and the like. These carriers may be used alone or in combination of at least two thereof.

Also, any other pharmaceutically acceptable additives such as an excipient, a diluent, an antioxidant, a buffer solution, or a bacteriostatic agent may be added to the pharmaceutical composition according to the present invention, if required. In addition, a filler, an extender, a humectant, a disintegrant, a dispersant, a surfactant, a binder, a lubricant, and the like may further be added thereto.

The pharmaceutical composition according to the present invention may be formulated into unit dosage forms suitable for oral or parenteral administration.

Non-limiting examples of formulations for oral administration may be troches, lozenges, tablets, aqueous suspensions, oily suspensions, prepared powders, granules, emulsions, hard capsules, soft capsules, syrups, or elixirs.

The pharmaceutical composition according to the present invention may be formulated for oral administration by using a binder such as lactose, sucrose, sorbitol, mannitol, amylopectin, cellulose, or gelatin; an excipient such as dicalcium phosphate; a disintegrant such as corn starch or sweet potato starch; and a lubricant such as magnesium stearate, calcium stearate, sodium stearyl fumarate, or polyethylene glycol wax, further with a sweetener, an aromatic agent, a syrup, and the like.

Furthermore, for capsule formulation, a liquid carrier such as fatty oil may further be added thereto in addition to the substances described above.

Non-limiting examples of formulations for parenteral administration may be injection solutions, suppository, powders for inhalation through the respiratory tract, aerosols for spraying, ointments, powders for skin, oils, or creams.

The pharmaceutical composition according to the present invention may be formulated for parenteral administration by using a sterile aqueous solution, a non-aqueous solvent, a suspension, an emulsion, a lyophilizate, a formulation for external use. Examples of the non-aqueous solvent and the suspension may be propylene glycol, polyethylene glycol, vegetable oils such as olive oil, and injectable esters such as ethyl oleate.

In addition, more particularly, the pharmaceutical composition according to the present invention is formulated into injectable formulations, the composition according to the present invention may be mixed with a stabilizer or a buffer in water to prepare a solution or suspension and then formulated into a unit dosage form of ampoules, vials, or the like. Also, when the pharmaceutical composition according to the present invention is formulated into aerosols, a propellant may further be mixed with the additives to disperse a water-dispersed concentration or wet powder is sprayed.

Since it was confirmed that the insulin receptor aptamer according to the present invention more effectively reduces a blood sugar level in vivo (Example 3-5), uptakes glucose in vitro (Example 3-6), and reduces lipolysis (Example 3-7) than insulin, the pharmaceutical composition including the aptamer as an active ingredient may be used for prevention or treatment of insulin-related diseases.

Another aspect of the present invention to achieve the objects of the present invention provides a method of preventing or treating an insulin-related disease, the method including administering a pharmaceutical composition containing the insulin receptor aptamer as an active ingredient to a subject except a human. The insulin receptor aptamer, the insulin-related disease, prevention, and treatment are as described above.

As used herein, the term "subject" refers to animals including mammals such as rats, livestock, and humans.

Administration routes and administration methods of the pharmaceutical composition according to the present invention may be independently adjusted, and any administration route and administration method may be used without limitation as long as the pharmaceutical composition arrives at a target region. The pharmaceutical composition may be administered orally or parenterally.

As a method for the parenteral administration may be intravenous administration, intraperitoneal administration, intramuscular administration, transdermal administration, or subcutaneous administration may be used, without being limited thereto.

A pharmaceutically effective amount and effective dosage of the pharmaceutical composition may vary according to preparation methods of the pharmaceutical composition, administration methods, administration durations, and/or administration routes and may also vary according to various factors and similar factors well known in the field of pharmaceuticals such as types and degrees of a response to be achieved by administering the pharmaceutical composition, types of individual as a subject, age, weight, general health conditions, symptom and severity of disease, gender, diet, excretion rate, ingredients of drug(s) administered in combination simultaneously or separately. A skilled practitioner may easily determine and prescribe a dosage effective for the desired treatment or prevention.

For more preferable effects of the pharmaceutical composition according to the present invention, an appropriate daily dose may be in the range of 0.0001 to 100 mg/kg (weight), preferably, in the range of 0.001 mg/kg to 10 mg/kg.

Thus, although an effective dosage of the pharmaceutical composition according to the present invention including the insulin receptor aptamer as an active ingredient is not particularly limited, the dosage of the pharmaceutical composition may be adjusted such that the insulin receptor aptamer is administered within the amount described above for desired effects.

The pharmaceutical composition according to the present invention may be administered once to several times a day in divided doses. The pharmaceutical composition according to the present invention may be administered as an individual therapeutic agent, in combination with other therapeutic agents, or sequentially or simultaneously with a conventional therapeutic agent(s). It is important to administer an amount to obtain the maximum effect with a minimum amount without adverse effects considering the factors described above, and the amount may easily be determined by one of ordinary skill in the art.

The pharmaceutical composition according to the present invention may be administered alone or in combination with methods using surgical operation, hormone therapy, drug therapy, and biological response regulators in order to prevent, relieve, or treat insulin-related diseases.

Another aspect of the present invention to achieve the objects of the present invention provides a composition for diagnosing diabetes or diabetic complications including the insulin receptor aptamer as an active ingredient.

As used herein, the term "diagnosis" refers to identifying the presence or characteristics of a pathological condition, particularly, the onset of diabetes or diabetic complications.

Also, the present invention provides a method of providing information for diagnosing of diabetes or diabetic complications using the insulin receptor aptamer.

The method of providing information for diagnosing diabetes or diabetic complications includes: preparing an isolated biological sample; reacting the biological sample with the insulin receptor aptamer according to the present invention; and measuring a binding degree of the insulin receptor aptamer in the biological sample, wherein the biological sample is diagnosed as diabetes when the binding degree of the insulin receptor aptamer in the biological sample is higher than that of a normal sample.

In the step of measuring the binding degree of the insulin receptor aptamer in the biological sample may be performed using a method commonly used to measure DNA aptamer binding in the art, for example, a method including labeling one end of the insulin receptor aptamer with a fluorescent or radioactive substance, and measuring intensity of fluorescence or radioactivity the substance or imaging thereof, without being limited thereto.

MODE OF INVENTION

Hereinafter, the present invention will be described in more detail with reference to the following examples and experimental examples. However, these examples and experimental examples are for illustrative purposes only and are not intended to limit the scope of the present invention.

In the present invention, in order to develop effective insulin receptor aptamers, IR-A48 aptamer (hereinafter, referred to as A48, Korean Patent Laid-open Publication No. 10-2017-0013178, SEQ ID NO: 1) conventionally known as an insulin receptor aptamer was modified by sequence optimization or chemical optimization. Through such modification, aptamers, as an effective active ingredient of therapeutic agents for insulin-related diseases such as diabetes, have been developed by improving effects such as binding affinity for the insulin receptor and stability in serum.

Example 1: Preparation of Insulin Receptor Aptamer with Improved Effect by Sequence Optimization of A48 (A48m)

To improve the effects of A48, sequence optimization was performed by partially modifying the sequence of A48. An A48 variant synthesized by the sequence optimization had higher binding affinity for the insulin receptor than the conventional A48, thereby obtaining an aptamer having better effects than the conventional insulin receptor aptamer. Sequences of primers used in the example are listed in Table 1 below.

TABLE 1

| Sequence list | Sequence | SEQ ID NO: |
|---|---|---|
| Insulin aptamer forward primer_F | 5'-GAGTGACCGTCCGCCTG-3' | 2 |
| Insulin aptamer reverse primer_R | 5'-GGCTGGTGGTGTGGCTG-3' | 3 |

Example 1-1: Synthesis of Library

For sequence optimization by partially modifying the sequence of A48, a library of modified sequences of A48, each having 9 random nucleotides was synthesized to identity nucleotides to be modified to improve effects.

Figure 1B:
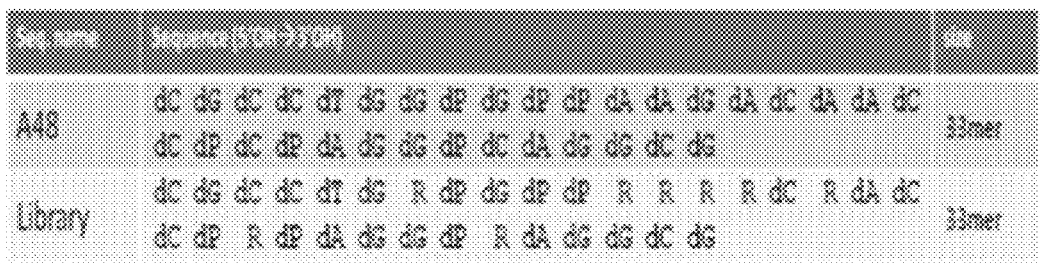
FIG. 1b is a library showing sequences used for preparing A48m (SEQ ID NO:1 and 13).

Particularly, an antisense library biotinylated at the 5'-end was synthesized to prepare a library needed for aptamer SELEX (FIG. 1). The antisense library was synthesized by reaction with 50 µM of the forward primer (SEQ ID NO: 2) at 70° C. for 2 hours with 1 mM dNTP (dATP, dGTP, dCTP, and Nap-dU), 0.25 U/µl KOD XL, and a 10× extension buffer (1.2 M Tris-HCl pH 7.8, 100 mM KCl, 60 mM $(NH_4)_2SO_4$, 70 mM $MgSO_4$, 1% TritonX100, 1 mg/ml BSA), thereby preparing double-stranded DNA. Single-stranded modified DNA was eluted using a 20 mM NaOH solution and then neutralized with a HCL solution. The prepared library was quantified using a 10% urea gel.

Example 1-2: Binding Reaction to Insulin Receptor

To select candidate sequences for an aptamer having excellent binding affinity for the insulin receptor from the synthesized library, binding reaction to the insulin receptor was performed.

Particularly, 1 nmole of the library synthesized as described above was incubated in a selection buffer (200 mM HEPES, 510 mM NaCl, 25 mM $MgCl_2$, and 25 mM KCl) for 5 minutes at 95° C., 70° C., 48° C., and 37° C., respectively, and mixed with a protein competitor buffer (10 µM prothrombin, 10 µM Casein, and 0.1% human serum albumin (HAS)), and then reacted with 10 mg/ml Hexa-His TALON beads (10 mg/ml Dynabeads® TALON™+1 mg/ml Hexa-Histidine beads) at 37° C. for 10 minutes after removing a supernatant.

After the selection, only the supernatant was transferred to a fresh tube and reacted at 37° C. for 1 hour with Dynabead TALON on which an insulin receptor protein was immobilized. The resultant was washed five times with 100 µl of a selection buffer (200 mM HEPES, 510 mM NaCl, 25 mM $MgCl_2$, and 25 mM KCl), the $5^{th}$ washing was performed after transferring the resultant to a fresh tube. A target-bound library was eluted by 85 µl of a 2 mM NaOH solution thereto, followed by neutralization with 20 µl of an 8 mM HCl solution.

Example 1-3: Amplification of Insulin Receptor-Bound Library DNA

To obtain the library DNA bound to the insulin receptor prepared in Example 1-2, the library DNA was amplified using quantitative polymerase chain reaction (QPCR). Particularly, each of the forward primer (SEQ ID NO: 2) used in the preparation of the library and the antisense library biotinylated at the 5'-end was mixed with 5 µM and 1 mM dNTP (dATP, dGTP, dCTP, and dTTP), 0.075 UM KOD, and 25 mM $MgCl_2$ to prepare 25 µl solutions and then mixed with 100 µl of the prepared library. The mixture was incubated once at 96° C. for 15 seconds, at 55° C. for 10 seconds, and at 70° C. for 30 minutes, and then incubation performed at 96° C. for 15 seconds and at 70° C. for 1 minute was repeated 20 times, thereby preparing a double-stranded library.

Example 1-4: Preparation of eDNA eDNA, abbreviated for enzymatic DNA, refers to an aptamer produced from a DNA template using a polymerase. The DNA library constructed by QPCR was immobilized on 25 µl of MyOne SA beads by mixing therewith at room temperature for 5 minutes. The library immobilized on the beads was reacted at 70° C. for 30 minutes with 500 pmole of the forward primer (SEQ ID NO: 2) with an extension buffer (1.2 M Tris-HCl pH 7.8, 100 mM KCl, 60 mM $(NH_4)_2SO_4$, 70 mM $MgSO_4$, 1% TritonX100, and 1 mg/ml BSA), 0.5 mM dNTP (dATP, dGTP, dCTP, and Nap-dU), and 0.0625 UM KOD, thereby synthesizing DNA including modified nucleotides. The synthesized eDNA was used in a subsequent round. A total of 8 SELEX rounds were conducted. For more selective binding with the progress of SELEX rounds, the DNA-insulin receptor protein complex diluted with a 10 mM Dextran sulfate solution by 1/200 was used from the $3^{rd}$ round. Binding conditions for the respective rounds are shown in Table 2 below.

TABLE 2

| SELEX ROUND | Binding condition (protein concentration (nm)) |
|---|---|
| 1R-2R | 50 nM |
| 3R-5R | 50 nM w/Kinetic Challenge |
| 6R-7R | 1 nM w/Kinetic Challenge |
| 8R | 500 pM w/Kinetic Challenge |

Example 1-5: Binding Affinity Assay of Round Pool

For binding affinity assay of each of sequence pools selected from each round with the insulin receptor, experiments for the binding affinity assay were performed using RI labeling and QPCR.

First, to perform binding affinity assay RI labeling, eDNA obtained from each round of the SELEX and labeled was added to a 1× SB17 buffer (200 mM HEPES, 510 mM NaCl, 25 mM $MgCl_2$, 25 mM KCl, and 5 mM EDTA) and heated and slowly cooled from 95° C. to 37° C. at a rate of 0.1° C./sec. After 7-point serial dilution of the insulin receptor protein was performed from 100 nM in the 1× SB17 buffer by 4.64 times, and 30 µl of eDNA was added thereto, followed by reaction at 37° C. for 30 minutes. A nylon membrane was spotted with 2 µl of each DNA and then added with 5.5 µl of Zorbax resin, followed by reaction for 1 minute. The resultant was added to a Durapore filter plate which was previously wetted with 30 µl of 1× SB17 buffer and treated in a vacuum. 100 µl of the 1× SB17 buffer was added thereto for washing in a vacuum. After the nylon filter and the Durapore plate were exposed overnight to a phosphorimager screen, and images thus formed thereon were quantitatively analyzed (FIG. 2).

As a result of binding affinity assay of pools of the SELEX rounds, it was confirmed that the pools from rounds 5, 6, and 7 had excellent binding affinity, and thus the pools from the rounds 5, 6, and 7 were subjected to base sequencing by Next Generation Sequencing (NGS).

Example 1-6: Base Sequencing of Selected Aptamer

The products of the rounds 5, 6 and 7 were amplified by PCR using the forward primer (SEQ ID NO: 2) and a reverse primer (SEQ ID NO: 3). The PCR products were subjected to Next Generation Sequencing (NGS) by using an Illumina NextSeq platform and an Illumina TruSeq Nano DNA LT Sample Preparation Kit.

Figures 3A, 3B:
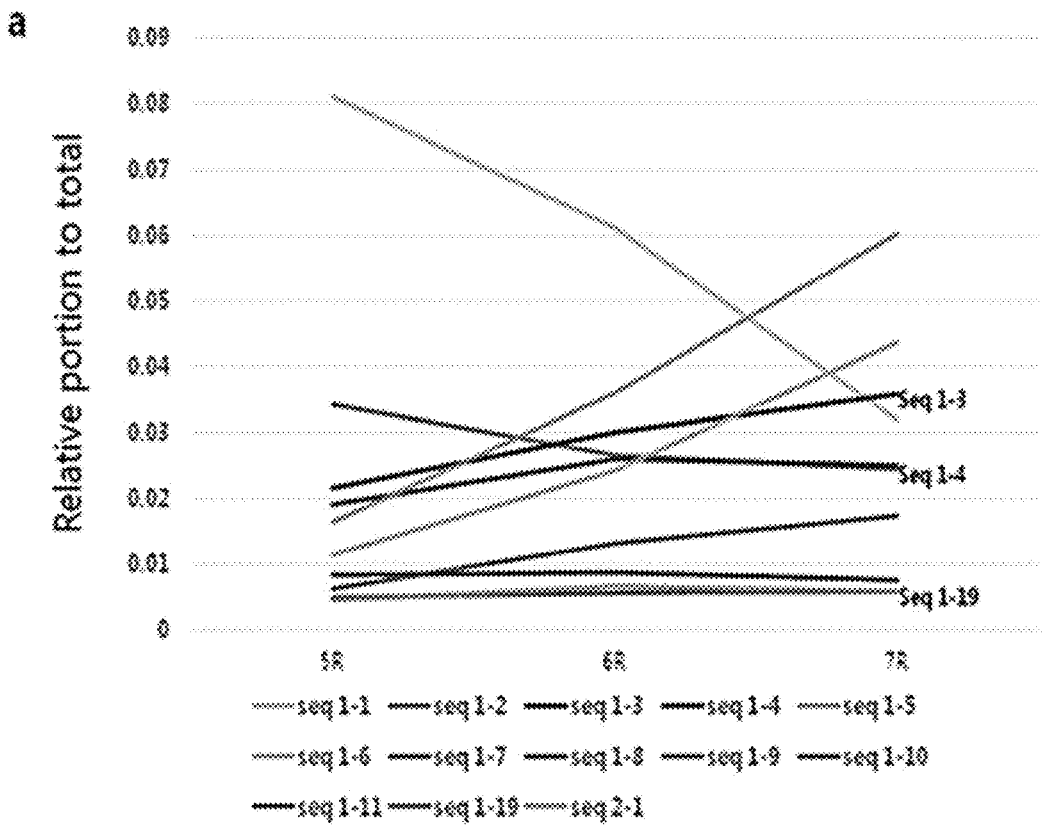
FIG. 3a shows proportions of sequences of each round with the progress of rounds.
FIG. 3b shows states of 12 candidate sequences (SEQ ID NOs: 14-26) in each round.

As a result, top 50 sequences having a large number reads present in each round pool were selected and changes in proportions of the sequences in each round were identified (FIG. 3). It was determined that sequences with increasing proportions with the progress of rounds contribute to improvement of binding affinity, and the sequences were selected. During this process, proportions of sequences 1-1, 1-2, 1-7, 1-8, and 1-10 decrease with the progress of rounds, and sequences 1-5, 1-6, 1-9, and 1-11 were contaminated by other sequences. Thus, sequences 1-3, 1-4, and 1-19 not corresponding thereto were selected as representative sequences having the effects of the pool, and the three aptamers 1-3, 1-4, and 1-19 were named A48 seq 1-3, A48 seq 1-4, and A48 seq 1-19, respectively. Sequences selected thereby are shown in Table 3.

TABLE 3

| Sequence list | Sequence | Size | SEQ ID NO: |
|---|---|---|---|
| A48 seq 1-3 | 5'-CGCCTGGPGPPCPAAACGA CCPCPAGGPAAGG-3' | 32 mer | 4 |
| A48 seq 1-4 | 5'-CGCCTGGPGPPAAGACAAC CPCPAGGPAAGGCT-3' | 33 mer | 5 |
| A48 seq 1-19 | 5'-CGCCTGGPGPPCPAGACGA CCPAPAGGPPAGGC-3' | 33 mer | 6 |

Example 1-7: Binding Affinity Assay of Selected Aptamer

To examine whether binding affinity of each of the selected three aptamers for the insulin receptor is better than that of the A48 aptamer, clone binding affinity assay was conducted.

Particularly, 10 fmole of each aptamer was added to a 1× SB18 buffer (200 mM HEPES, 510 mM NaCl, 25 mM $MgCl_2$, and 25 mM KCl) and reacted at 95° C., 70° C., 48° C., and 37° C. for 5 minutes each. Then, after 7-point serial dilution of the insulin receptor protein was performed from 100 nM in the 1× SB18 buffer by 4.64 times, and 30 μl of the aptamer was added thereto, followed by reaction at 37° C. for 30 minutes. 5.5 μl of Dynabead TALON was added to the aptamer-protein complex, followed by reaction at room temperature for 5 minutes. The resultant was added to a Durapore filter plate which was previously wetted with 30 μl of the 1× SB18 buffer and treated in a vacuum. 100 μl of the 1× SB18 buffer was added thereto for washing in a vacuum. Then, the aptamer-protein complex was eluted with a 2 mM NaOH solution at room temperature for 5 minutes, followed by neutralization with a 8 mM HCl solution.

Figure 4:
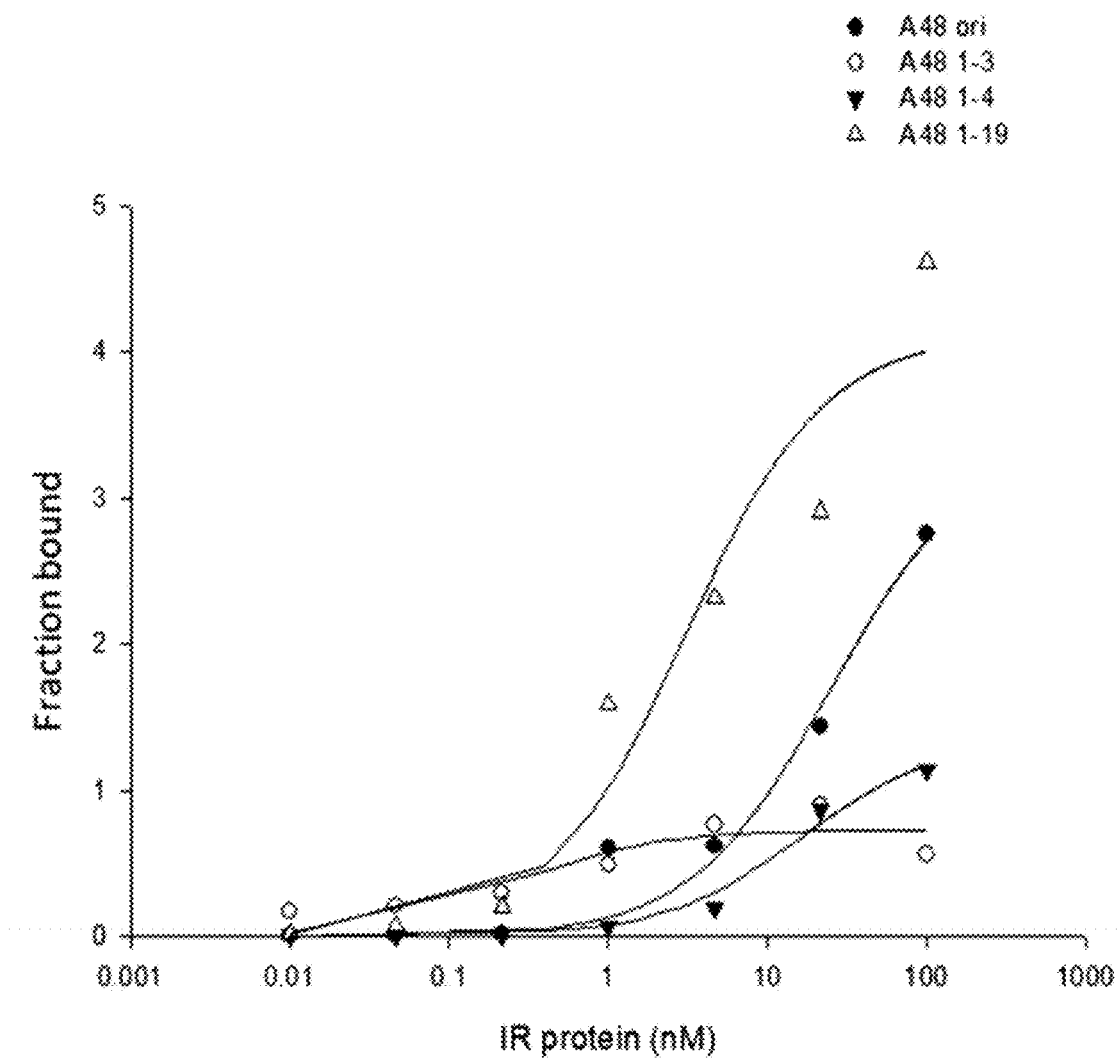
FIG. 4 shows binding affinity of A48m candidate sequences for insulin receptor protein.

The aptamer-protein complex obtained as described above was amplified by QPCR. The forward primer (SEQ ID NO: 2) and the reverse primer (SEQ ID NO: 3) in a concentration of 0.2 μM, 0.2 μM dNTP (dATP, dGTP, dCTP, and dTTP), 5 mM $MgCl_2$, 0.025 UM KOD XL and the DNA-protein complex were mixed such that a total volume thereof was 20 μl. The mixture was incubated once at 96° C. for 15 seconds, at 55° C. for 10 seconds, and at 70° C. for 30 minutes, and then incubation performed at 96° C. for 15 seconds, at 55° C. for 10 seconds, and at 70° C. for 1 minute was repeated 40 times for amplification. After normalization of Ct values as a standard, Kd and Bmax values were calculated by using a SigmaPlot (FIG. 4).

As a result, it was confirmed that all of the three aptamers had higher Kd values for the insulin receptor than the conventional A48 and the A48 seq 1-19 also had a higher Bmax value than that of the A48. Thus, it was confirmed that the A48 seq 1-19 had the highest binding affinity among the selected three aptamers. Accordingly, the A48 seq 1-19 was selected as a final variant by sequence optimization and named A48m.

Example 1-8: Identification of In Vivo Activity of A48m

To identify in vivo activity of the A48m as an insulin receptor aptamer in vivo, an insulin tolerance test (ITT) was conducted on normal rats and streptozotocin (STZ)-induced type 1 diabetic rats. Particularly, after fasting 8-week old male C57Bl/6J rats for 12 hours, A48m dissolved in PBS was administered by intraperitoneal injection to the rats for the experiment at a dose of 10 mg/kg. Blood was collected from tails of the rats at 15 minutes, 30 minutes, 60 minutes, 90 minutes, 120 minutes, and 180 minutes after administration and changes in blood sugar level thereof were observed using a blood sugar monitoring device (Accu-Check Active; Roche Diagnostics).

As a result, it was confirmed that the A48m aptamer efficiently decreased the blood sugar level in the type 1 diabetic rat model. In addition, hypoglycemia was not observed in the normal rats, either. Thus, it was confirmed that the A48m aptamer has an excellent effect on reducing the blood sugar level (FIG. 5).

Example 2: Improvement of Properties of A48m by Chemical Optimization

An aptamer having a better effect than the conventional A48 was developed by sequence optimization in Example 1 described above and subjected to a chemical optimization process for further improvement of the effect of the aptamer. A chemical variant of the A48m synthesized thereby had increased insulin receptor phosphorylation activity and improved serum stability than the A48m.

Example 2-1: Identification of Effect of Chemical Modification of Each Nucleotide of A48m Sequence Among the A48 seq 1-3, the A48 seq 1-4, and the A48 seq 1-19 (A48m) prepared according to Example 1, the A48m consisting of 33 nucleotides, as a representative example, was modified by modifying each of 25 nucleotides, except for naphthyl uracil (P), with 2'-OMe ($N_{me}$), C3-linker (L), or 2'-F ($N_f$), thereby preparing a total of 75 chemical variant samples of the A48m. Also, 8 additional chemical variant samples of the A48m were prepared by modifying each of the 8 naphthyl uracils (Ps) with benzyl uracil (Z).

Example 2-2: Identification of Insulin Receptor Phosphorylation Activity of Chemical Variant Sample of A48m To identify the insulin receptor phosphorylation activity of the chemical variant samples of A48m prepared in Example 2-1, an experiment was performed as follows. Particularly, Rat-1/hIR cells were seeded on a 12-well plates at a density of $10^5$ cells per well and cultured overnight in a high glucose Dulbecco's modified Eagle's medium (DMEM) supplemented with 10% fetal bovine serum (FBS). The cells untreated with the aptamer samples were incubated in the DMEM not including FBS for 3 hours, washed three times with 1×PBS, and incubated in a Krebs-Ringer HEPES buffer [25 mM HEPES (pH 7.4), 120 mM NaCl, 5 mM KCl, 1.2 mM $MgSO_4$, 1.3 mM $CaCl_2$, and 1.3 mM $KH_2PO_4$] for 1 hour. The aptamer samples, which were the chemical variants of A48m prepared in Example 2-1, were heated at 95° C. for 5 minutes and cooled at room temperature such that a three-dimensional structure of each aptamer was reconstructed. The aptamers were dissolved in the Krebs-Ringer HEPES buffer for preparation.

The aptamer samples were added to each well of the 12-well plate and incubated for 1 hour. After 1 hour, the plate was washed three times with 1×PBS and the cells were isolated from the plate and lysed with a lysis buffer. The cell lysates were centrifuged at 4° C. at 14,000 rpm for 15 minutes to isolate proteins. The isolated samples were heated at 100° C. for 5 minutes with a 5× sample buffer and slowly cooled at room temperature to prepare western blot samples. The prepared samples were subjected to electrophoresis on 4%-12% SDS-PAGE for 1 hour and 30 minutes and transferred to a nitrocellulose membrane for 1 hour and 30 minutes. Then, the membrane was blocked at room temperature for 40 minutes in a blocking buffer solution (1×PBST, 3% skim milk) and incubated for 1 hour at room temperature with a primary antibody [anti-phosphor-IR (10C3), Santa Cruz Biotechnology or anti-β-actin (D6A8), Cell Signaling Technology] diluted in a blocking buffer at 1:500 or 1:1000. The membrane was washed three times with 1×PBS and incubated for 1 hour at room temperature with a secondary binding antibody diluted in the blocking buffer at 1:20000, and washed three times with 1×PBST. An ECL solution was sprayed onto the membrane, followed by incubation at room temperature for 1 minute and exposure to x-rays. Intensities of bands formed on the membrane were quantified via comparison with A48m.

As a result, different degrees of insulin receptor phosphorylation were observed according to positions of nucleotides and types of chemical modification, and the degrees of phosphorylation were shown in Tables 4 and 5 below based on the degree of phosphorylation of A48m that is not chemically modified.

TABLE 4

| (SEQ ID NO: 6) IR Phosphorylation (Fold of A48m) at 200 nM treatment | | | | | | | | | | | | | | | | |
|---|---|---|---|---|---|---|---|---|---|---|---|---|---|---|---|---|
| | C | G | C | C | T | G | G | P | G | P | P | C | P | A | G | A | C |
| A48m | 1 | 1 | 1 | 1 | 1 | 1 | 1 | 1 | 1 | 1 | 1 | 1 | 1 | 1 | 1 | 1 | 1 |
| C3-Linker | 0.90 | 0.97 | 0.31 | 0.24 | 0.33 | 0.22 | 0.34 | — | 0.22 | — | — | 1.7 | — | 0.15 | 0.24 | 0.91 | 0.86 |
| 2'-methoxy | 0.92 | 1.28 | 0.88 | 0.96 | 0.89 | 0.75 | 0.22 | — | 0.08 | — | — | 0.65 | — | 0.91 | 0.86 | 0.88 | 0.89 |
| 2'-F | 0.97 | 1.12 | 0.84 | 0.94 | 0.92 | 0.98 | 0.64 | — | 0.96 | — | — | 0.73 | — | 0.89 | 0.85 | 1 | 0.78 |
| Benzyl | — | — | — | — | — | — | — | 0 | — | 2.7 | 0 | — | 1 | — | — | — | — |
| | G | A | C | C | P | A | P | A | G | G | P | P | A | G | G | C |
| A48m | 1 | 11 | 1 | 1 | 1 | 1 | 1 | 1 | 1 | 1 | 1 | 1 | 1 | 1 | 1 | 1 |
| C3-Linker | 1.16 | 0.15 | 0.08 | 0.06 | — | 0.23 | — | 0.12 | 0.14 | 0.05 | — | — | 0.32 | 0.13 | 0.36 | 0.84 |
| 2'-methoxy | 0.57 | 0.96 | 0.49 | 0.97 | — | 0.92 | — | 0 | 0.03 | 1.01 | — | — | 0.86 | 1.2 | 1.11 | 0.89 |
| 2'-F | 0.7 | 0.94 | 1.06 | 0.97 | — | 0.77 | — | 0.41 | 0.04 | 1.11 | — | — | 0.95 | 1.1 | 1.09 | 0.89 |
| Benzyl | — | — | — | — | 0.01 | — | 0 | — | — | — | 1.09 | 0.9 | — | — | — | — |

TABLE 5

| (SEQ ID NO: 6) IR Phosphorylation (Fold of A48m at 200 nM treatment | | | | | | | | | | | | | | | | |
|---|---|---|---|---|---|---|---|---|---|---|---|---|---|---|---|---|
| | C | G | C | C | T | G | G | T | G | T | T | C | T | A | G | A | C |
| A48m | 1 | 1 | 1 | 1 | 1 | 1 | 1 | 1 | 1 | 1 | 1 | 1 | 1 | 1 | 1 | 1 | 1 |
| C3-Linker | 1.27 | 0.5 | 0.11 | 0.11 | 0.11 | 0.08 | 0.09 | — | 0.06 | — | — | 1.08 | — | 0.26 | 0.36 | 0.89 | 0.66 |
| 2'-methoxy | 1.19 | 1.31 | 0.95 | 1.11 | 3.41 | 0.45 | 0.03 | — | 0.05 | — | — | 0.47 | — | 1.81 | 0.6 | 3.32 | 0.72 |
| 2'-F | 1.27 | 0.87 | 1.02 | 1.13 | 2.56 | 0.63 | 0.58 | — | 0.55 | — | — | 1.03 | — | 1.42 | 0.45 | 2.13 | 1.1 |
| Benzyl | — | — | — | — | — | — | — | 0.14 | — | 0.83 | 0.16 | — | 0.9 | — | — | — | — |
| | G | A | C | C | T | A | T | A | G | G | T | T | A | G | G | C |
| A48m | 1 | 1 | 1 | 1 | 1 | 1 | 1 | 1 | 1 | 1 | 1 | 1 | 1 | 1 | 1 | 1 |
| C3-Linker | 1.19 | 0.17 | 0.13 | 0.07 | — | 0.18 | — | 0.06 | 0.06 | 0.06 | — | — | 0.11 | 0.08 | 0.14 | 0.58 |
| 2'-methoxy | 0.36 | 3.47 | 0.2 | 1.04 | — | 2.67 | — | 0.13 | 0.02 | 1.02 | — | — | 1.69 | 1.24 | 1.14 | 0.64 |
| 2'-F | 0.35 | 2.92 | 1.59 | 1.24 | — | 1.32 | — | 0.15 | 0.08 | 0.88 | — | — | 1.44 | 1.01 | 1.00 | 1.13 |
| Benzyl | — | — | — | — | 0.33 | — | 0.24 | — | — | — | 0.95 | 0.77 | — | — | — | — |

Example 2-3: Selection of Chemical Variant of A48m by Combining Chemical Modifications of A48m Based on the degrees of insulin receptor phosphorylation activities according to chemically modified nucleotides of the A48m sequence prepared in Example 2-2, various experiments of combining the chemically modified positions were performed and 5 candidate sequences for an aptamer predicted to be chemically optimized were selected. Since the candidate sequences were selected in consideration of the degrees of phosphorylation activity and stability of the aptamers focusing on improvement of stability, selection of the candidate sequences was performed by prioritizing a higher stability unless a significant decrease in phosphorylation activity was caused. A level of contribution to improvement of stability generally decreases in the order linker>methoxylation>fluoridation, and thus a sequence modified with a linker was selected in the case where phosphorylation activities were similar.

Additionally, since methoxylation causes from RNA, methoxy-uracil is more common than methoxy-thymine when thymine of the A48m is methoxylated. Thus, methoxylation was conducted after modifying thymine to uracil present in RNA.

The candidate sequences were aptamers each having a nucleotide sequence in which two nucleotides (CG) of the 5'-end and one nucleotide (C) at the 3'-end of the A48m are absent in common and named A48m combi 1 to A48m combi 5, respectively.

Example 3: Identification of Activity of Chemically Optimized A48m as Insulin Receptor Aptamer

Figure 6A:
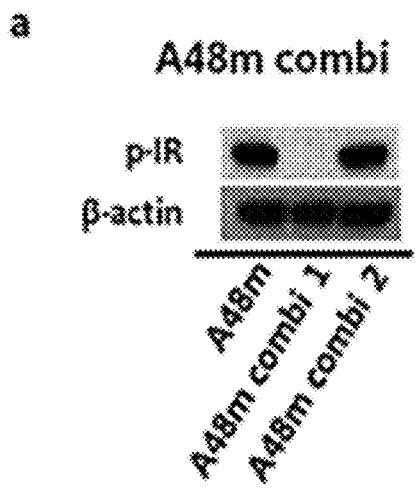
FIG. 6a shows insulin receptor phosphorylation activity of A48m combi 1.
Figure 6B:
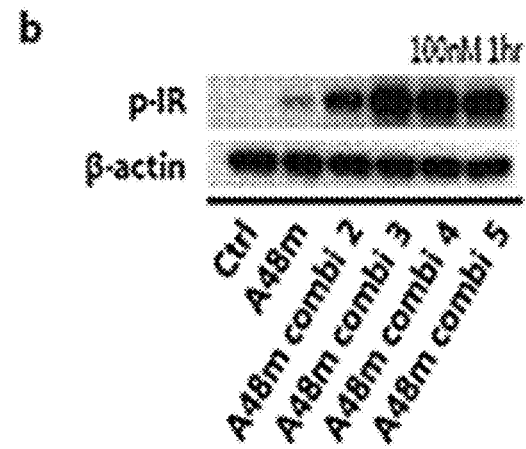
FIGS. 6b to 6d show insulin receptor phosphorylation activity of A48m combi 2 to A48m combi 5.
Figure 6C:
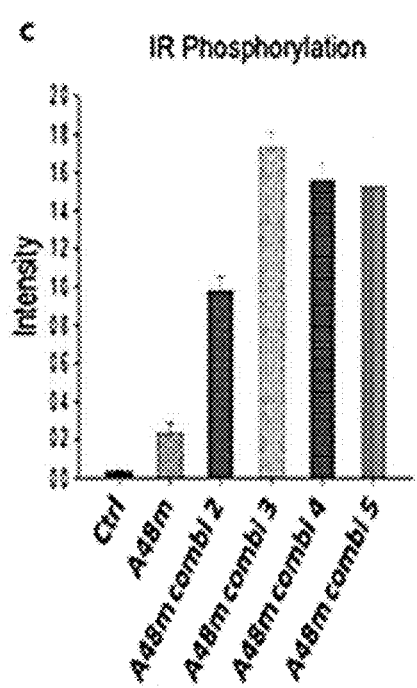
Figure 6D:
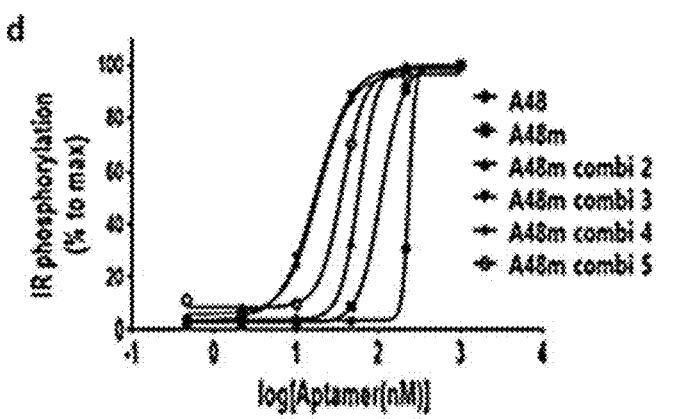

Example 3-1: Identification of Ability of Insulin Receptor Phosphorylation Activity of Chemically Optimized Candidate Sequence of A48m As a result of identifying the ability of each of the A48m combi 1 to the A48m combi 5, which are 5 candidate sequences selected in Example 2, to increase the degrees of phosphorylation of the insulin receptor, it was confirmed that the A48m combi 1 cannot increase the degree of phosphorylation of the insulin receptor (FIG. 6a), while the other A48m combi 2 to A48m combi 5 exhibited better effects than the A48m (FIGS. 6b to 6d). Thus, the following experiments were conducted using the A48m combi 2 to A48m combi 5 except for the A48m combi 1. Sequences of the A48m combi 2 to A48m combi 5 are shown in Table 6 below.

TABLE 6

| CHEMICAL VARIANT | SEQUENCE | SEQ ID NO: |
|---|---|---|
| A48m combi 2 | 5'-$C_{me}C_{me}U_{me}$GGPGZPLPA$_{me}$GLLGA$_{me}$C$_f$C$_{me}$PA$_{me}$PAGG$_{me}$ZPA$_{me}$G$_{me}$G$_{me}$-idT | 7 |
| A48m combi 3 | 5'-$C_{me}C_{me}U_{me}$GGPGZPLPA$_{me}$GA$_{me}$C$_f$G A$_{me}$C$_f$C$_{me}$PA$_{me}$PAGG$_{me}$PPA$_{me}$G$_{me}$G$_{me}$-idT | 8 |
| A48m combi 4 | 5'-$C_{me}C_{me}U_{me}$GGPGZPLPA$_{me}$GA$_{me}$C$_f$GL C$_f$C$_{me}$PA$_{me}$PAGG$_{me}$PPA$_{me}$G$_{me}$G$_{me}$-idT | 9 |
| A48m combi 5 | 5'-$C_{me}C_{me}U_{me}$GGPGZPLPA$_{me}$GLLGA$_{me}$C C$_{me}$PA$_{me}$PAGG$_{me}$PPA$_{me}$G$_{me}$G$_{me}$-idT | 10 |

In addition, insulin receptor phosphorylation activity was identified in the case where methoxy-uracil was substituted with methoxy-thymine in the aptamers.

Figure 6E:
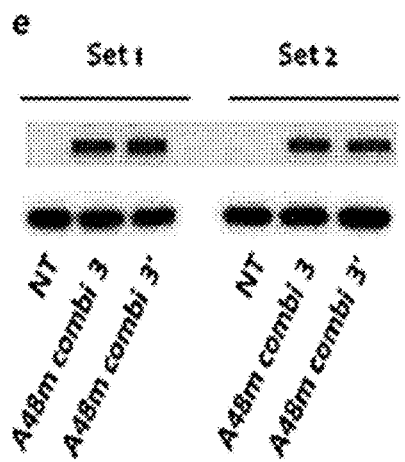
FIGS. 6e and 6f show insulin receptor phosphorylation activity of A48m combi 3'.
Figure 6F:
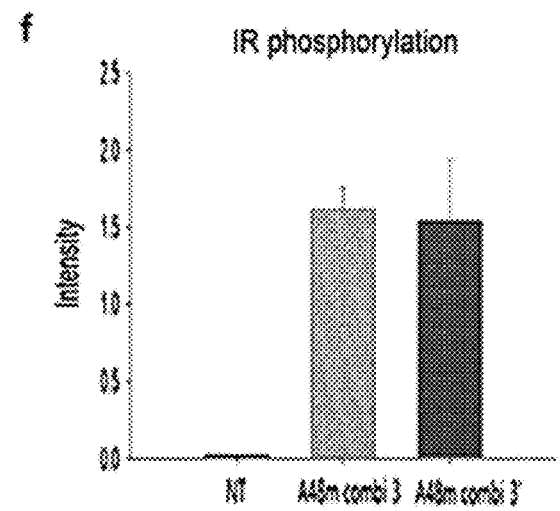

Particularly, the A48m combi 3 in which methoxy-uracil was modified to methoxy-thymine was named A48m combi 3' and the degree of phosphorylation of the insulin receptor using the same was identified. Thus, it was confirmed that the degrees of insulin receptor phosphorylation were similar when using the A48m combi 3 and the A48m combi 3' (FIGS. 6e and 6f). Thus, it can be seen that mutual substitution between thymine and uracil does not affect functions of the aptamers according to the present invention.

Example 3-2: Identification of Stability of Aptamer in Serum

Serum stability of each of the A48m combi 2 to A48m combi 5 was identified, except for the A48m combi 1 not having insulin receptor phosphorylation as described in Example 3-1. The serum stability refers to a degree of being stable in vivo when the aptamer is administered as a therapeutic agent. As the serum stability is improved, the aptamer exists for a longer time in vivo, thereby increasing duration of action and increasing a dosing interval.

Particularly, 10 µl of a 10 µM aptamer was added to 45 µl of a 100% serum, followed by incubation at 37° C. for 0 hour, 4 hours, 24 hours, 48 hours, and 72 hours, respectively. After incubation, 5 µl of a 10 µM control aptamer was added thereto and diluted with 165 µl of distilled water. The same volume of a mixture of phenol, chloroform, isoamyl alcohol (phenol:chloroform:isoamyl alcohol=25:24:1) was added to the sample and gently mixed, and then centrifuged for 10 minutes at 16,000 g. After the centrifugation, a supernatant was transferred to a fresh tube and a 5× sample buffer was added thereto, followed by heat treatment at 95° C. for 5 minutes. The sample was subjected to electrophoresis on an urea gel for 25 minutes at 220V. The gel was stained with a SYBR gold to identify the gel using a Gel Doc™ EZ System infrared imaging system.

Figure 7A:
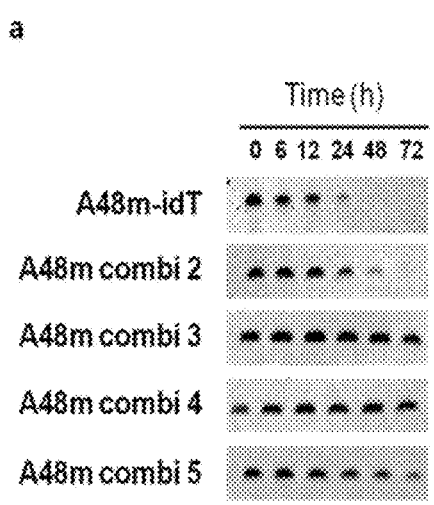
FIG. 7A-B shows serum stability of A48m combi 2 to A48m combi 5.
Figure 7B:
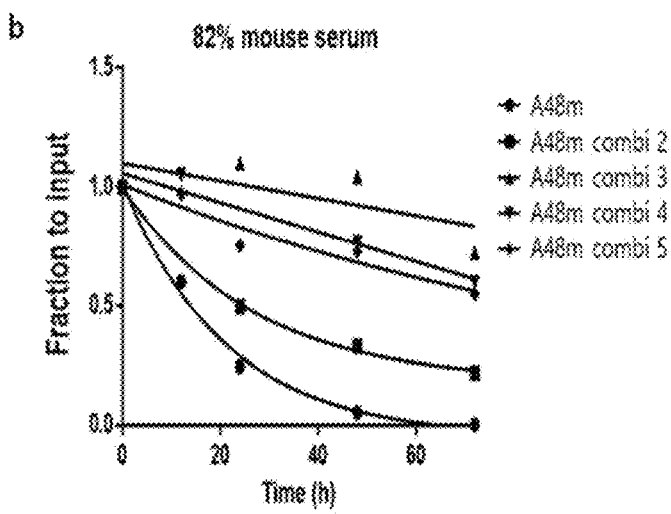

As a result of evaluating the serum stability, all of the A48m combi 2 to A48m combi 5 aptamers exhibited better serum stability than the A48m, and thus it was confirmed that they have stable activity in vivo as therapeutic agents for diabetes (FIG. 7).

Example 3-3: Identification of Selective Phosphorylation of Insulin Receptor In order to identify selective phosphorylation of the insulin receptor of the A48m combi 3 to A48m combi 5 aptamers, which exhibited excellent effects in the serum stability experiment of Example 3-2 above, phosphorylation activity of each of 6 tyrosine regions (Y960, Y1146, Y1150, Y1151, Y1316 and Y1322) of intracellular regions of the insulin receptor was evaluated by western blotting using various types of insulin receptor phosphorylation antibodies. For reference, since a phosphorylation antibody of Y953 was not developed, the experiment was performed except for the region.

Particularly, insulin receptor phosphorylation activity was identified by western blotting using anti-phosphor-IR antibody (Y1150/Y1151, 10C3, Santa Cruz Biotechnology), anti-phosphor-IR antibody (Y960, Invitrogen), anti-phosphor-IR antibody (Y1146, Invitrogen), anti-phosphor-IR antibody (Y1316, Invitrogen), anti-phosphor-IR antibody (Y1322, Invitrogen), anti-phosphor-IR antibody (Py, 4G10, Millipore), anti-IR-antibody (Santa Cruz, CA, USA), and anti-6-actin (D6A8, Cell Signaling Technology) as primary antibodies as described in Example.

Figure 8:
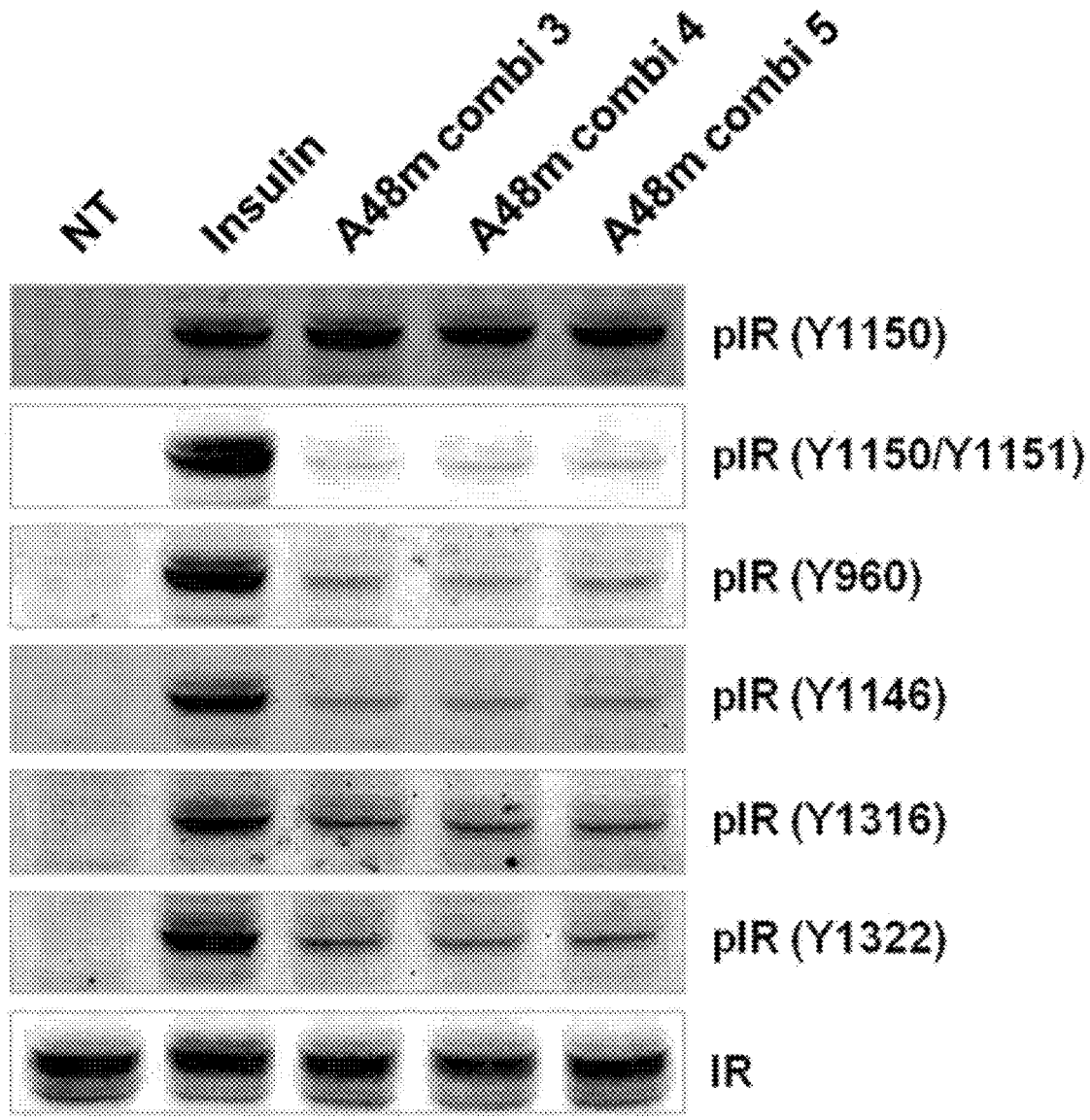
FIG. 8 shows selective phosphorylation activity of A48m combi 3 to A48m combi 5.

As a result, it was confirmed that although insulin has phosphorylation activity at all regions of Y960, Y1146, Y1150, Y1151, Y1316, and Y1322, the A48m combi 3 to A48m combi 5 aptamers have phosphorylation activity only at the Y1150 region (FIG. 8).

Example 3-4: Phosphorylation of Insulin Signaling Protein

Since it was confirmed that the A48m combi 3 to A48m combi 5 aptamers induce phosphorylation of only Y1150 among the various tyrosines of insulin in Example 3-3, an effects of the selective phosphorylation on a downstream signaling pathway of insulin was identified.

Particularly, completely differentiated 3T3-L1 cells were treated with 200 nM A48m combi 3 aptamer that was heated at 95° C. for 5 minutes and cooled at room temperature in Example 2, and samples thereof were subjected to western blotting using anti-phosphor-AKT antibody (T308), anti-phosphor-AKT antibody (S473), and anti-phosphor-ERK antibody (T202/Y204) as primary antibodies to identify phosphorylation of insulin signaling protein.

Figure 9:
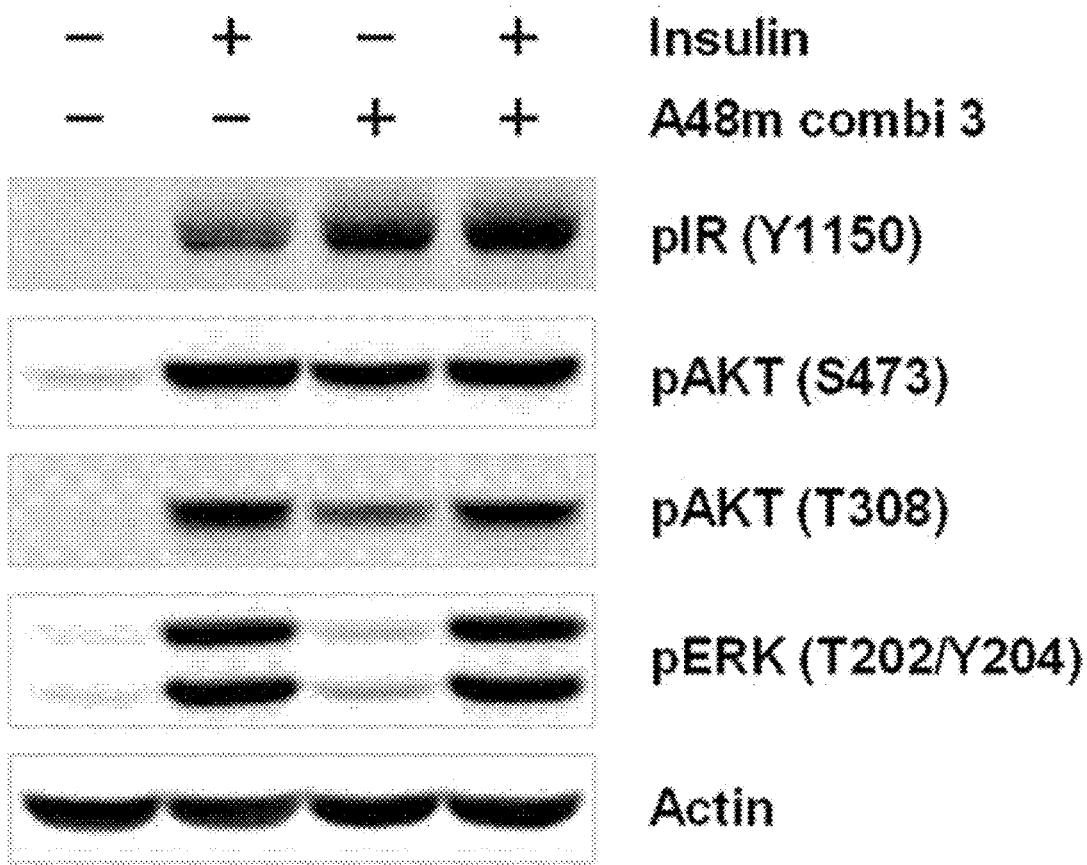
FIG. 9 shows phosphorylation activity of a downstream signaling pathway of A48m combi 3 in differentiated 3T3-L1 cells.

As a result, while phosphorylation was identified at the AKT S473 region, phosphorylation was not observed at the AKT T308 region and the ERK protein (T202/Y204) region unlike insulin (FIG. 9).

Based on the results, it can be seen that selective phosphorylation of the insulin receptor by the A48m combi 3 aptamer induces selective phosphorylation of the insulin signaling protein.

Example 3-5: Identification of In Vivo Blood Sugar Level Decrease Activity of Chemically Optimized A48m To identify whether the chemically optimized A48m aptamers (A48m combi 2 to 5) have in vivo activity as insulin receptor aptamers, an insulin tolerance test (ITT) was performed on normal rats and streptozotocin (STZ)-induced type 1 diabetic rats according to the method described in Example 1-8 above.

Particularly, after fasting 8-week old male C57Bl/6J rats for 12 hours, the A48m combi aptamers dissolved in PBS were administered by intraperitoneal injection to the rats for the experiment at a dose of 10 mg/kg. Blood was collected from tails of the rats at 15 minutes, 30 minutes, 60 minutes, 90 minutes, 120 minutes, and 180 minutes after administration and changes in blood sugar level thereof were observed using a blood sugar monitoring device (Accu-Check Active; Roche Diagnostics).

Figure 10A:
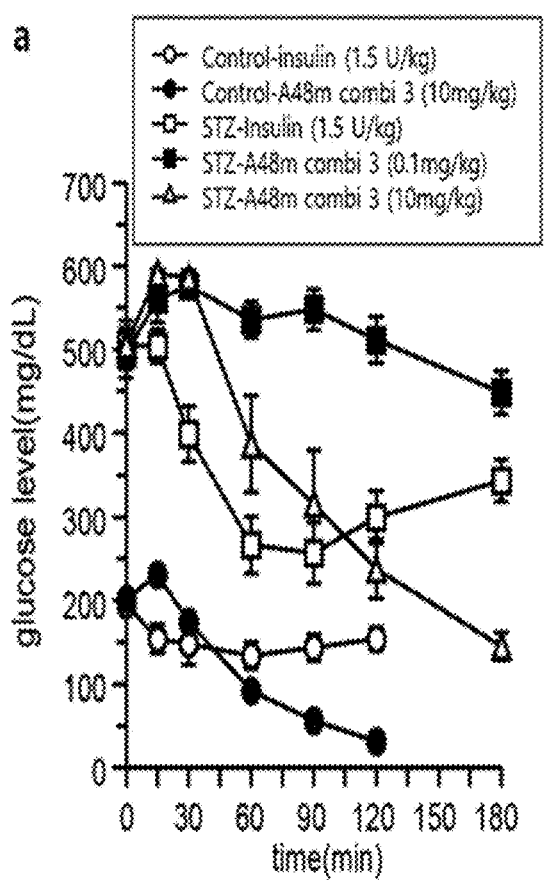
FIG. 10A-B shows an effect of A48m combi 3 aptamer on reducing the blood sugar level in vivo blood sugar level.

As a result, it was confirmed that the A48m combi 3 aptamer efficiently decreased the blood sugar level in the type 1 diabetic rat model than insulin. Thus, it was confirmed that the A48m combi 3 aptamer has an excellent effect on reducing the blood sugar level (FIG. 10a).

Figure 10B:
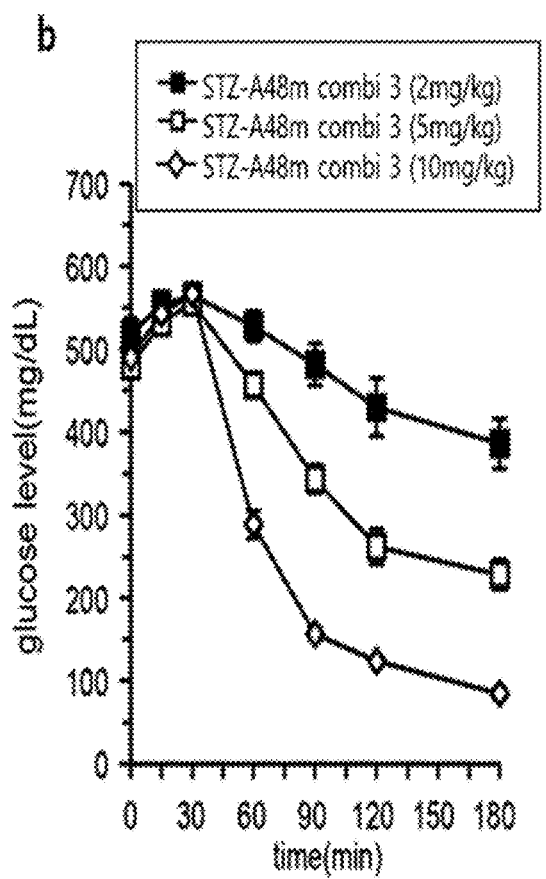

In addition, as a result of administering the A48m combi 3 aptamer to the type 1 diabetic rat model at doses of 2 mg/kg, 5 mg/kg, and 10 mg/kg and observing changes in blood sugar level, a concentration-dependent decrease in blood sugar level was observed (FIG. 10b).

Example 3-6: Identification In Vitro Glucose Uptake Activity of Chemically Optimized A48m To identify whether the chemically optimized A48m aptamers (A48m combi 2 to 5) have glucose uptake activity as insulin receptor aptamers in a normal state or in an insulin resistant state, an in vitro glucose uptake experiment was conducted using completely differentiated 3T3-L1 adipocytes.

Particularly, untreated, completely differentiated 3T3-L1 adipocytes were defined as the normal state, and the completed differentiated 3T3-L1 adipocytes were treated with 10 ng/ml TNF-α to induce the insulin resistant state, and then the experiments were performed.

For serum deficiency, the completely differentiated 3T3-L1 adipocytes were treated with DMEM with no FBS for 3 hours and treated with a Krebs-Ringer HEPES buffer solution for 1 hour. Subsequently, the adipocytes were treated respectively with insulin or the A48m combi 3 aptamer in concentrations of 1.6 nM, 8 nM, 40 nM, 200 nM, and 1000 nM for a given time and then treated with 2-deoxy[14C] glucose (0.1 µCi/ml) for 10 minutes. The resultant was washed three times with PBS supplemented with 20 mM glucose and the cells were dissolved using a solution including 0.5 N NaOH and 1% SDS. An amount of 2-Deoxy-D-glucose absorbed into the cells was observed using a liquid scintillation counter.

Figure 11A:
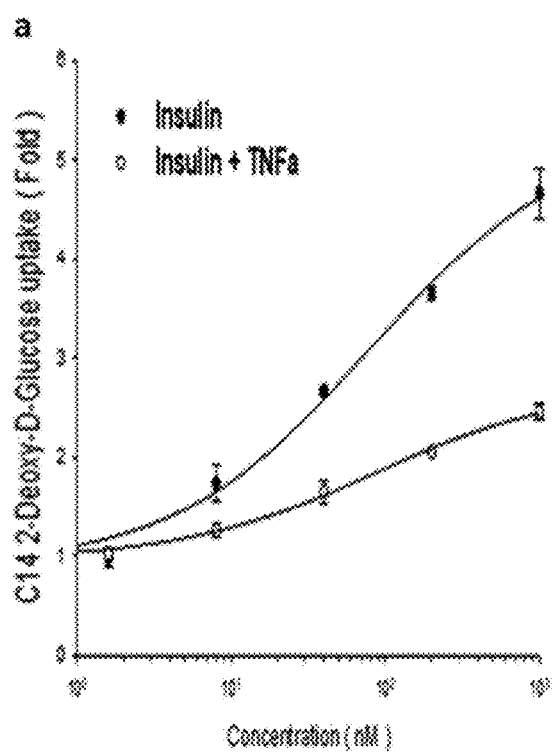
FIG. 11A-B shows an effect of A48m combi 3 aptamer on in vitro glucose uptake.
Figure 11B:
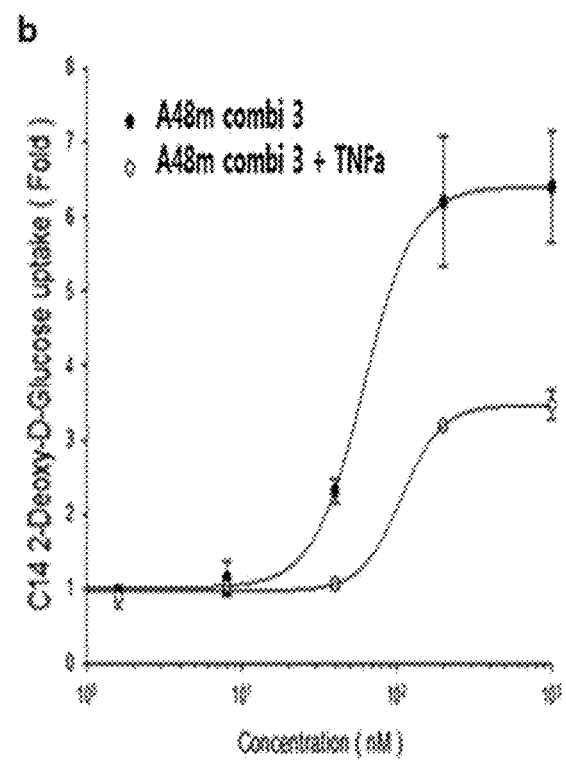

As a result, since glucose uptake rates obtained by using the A48m combi 3 both in the normal state and the insulin resistant state were similar to those obtained by using insulin (FIG. 11), and thus it was confirmed that the aptamer according to the present invention has a similar glucose uptake effect to that of insulin.

Example 3-7: Identification of Lipolysis Inhibition Activity of Chemically Optimized A48m To identify the effect of the chemically optimized A48m (A48m combi 2 to 5) on lipolysis inhibition as insulin receptor aptamers, an amount of glycerol released in a lipolysis process was measured by using completely differentiated 3T3-L1 adipocytes.

Particularly, for serum deficiency, the completely differentiated 3T3-L1 adipocytes were treated with DMEM with no FBS for 3 hours and treated with a Krebs-Ringer HEPES buffer solution for 1 hour to induce lipolysis caused by deficiency of glucose. The adipocytes were treated respectively with insulin or the A48m combi 3 aptamer in concentrations of 0.93 nM, 2.59 nM, 7.26 nM, 20.34 nM, 56.94 nM, 159.44 nM, 446.43 nM, 1250 nM, and 3500 nM for 4 hours, and then a buffer used to treat the cells was collected. 20 µl of the collected buffer was added to a 96-well plate and 200 µl of a free glycerol reagent (Sigma F6428) was added thereto, followed by reaction at room temperature for 30 minutes. Then, concentration-dependent color development of glycerol released from the cells was measured by measuring absorbance at 540 nm.

Figure 12A:
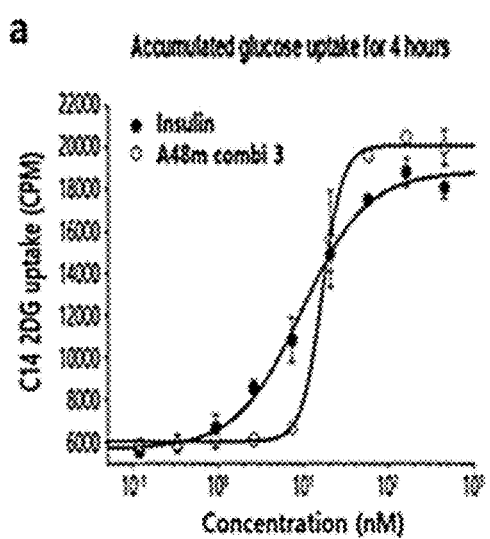
FIG. 12A-C shows an effect of A48m combi 3 aptamer on inhibiting lipolysis.
Figure 12B:
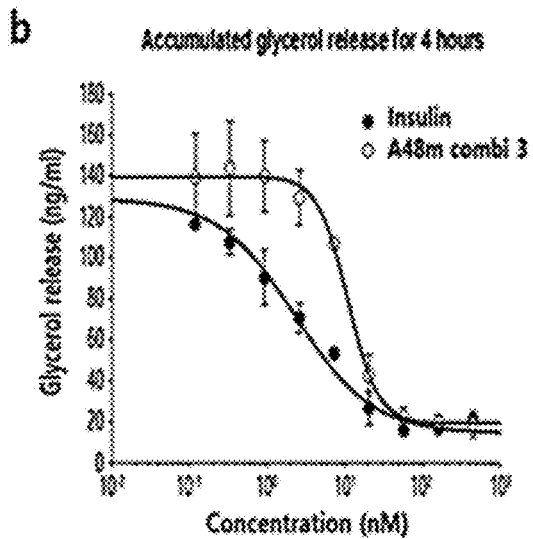
Figure 12C:
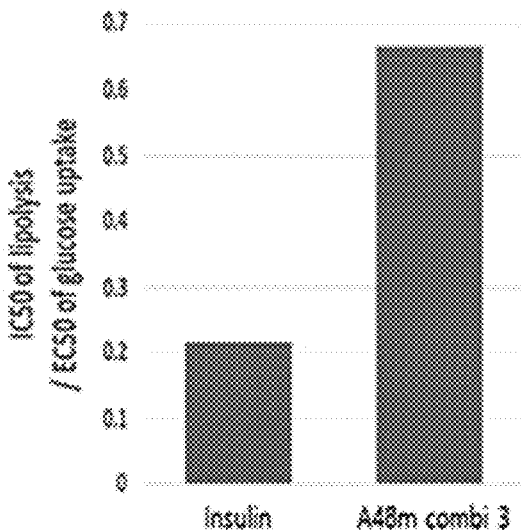

As a result, while insulin showed a difference of 4.6 times between a glucose uptake EC50 (9.6 nM) and a lipolysis IC50 (2.07 nM), the A48m combi 3 showed a difference of 1.5 times between a glucose uptake EC50 (16.5 nM) and a lipolysis IC50 (11 nM) (FIG. 12). Thus, it can be seen that the aptamer according to the present invention has a relatively lower lipolysis inhibition effect when compared with the glucose uptake activity, indicating that the aptamer according to the present invention has a lower lipolysis inhibiting effect than insulin in a situation where glucose uptake is induced.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:

1. An insulin receptor aptamer comprising a nucleotide sequence of General Formula 1 below:

5'-R1-R2-C-C-R3-G-G-P-G-R4-P-R5-P-A-R6-R7-R8-G-A-C-C-P-R9-P-A-G-G-R10-R11-A-G-G-R12-3'     General Formula 1 (SEQ ID NO:11)

R1 is a cytosine nucleotide (C) or absent;
R2 is a guanine nucleotide (G) or absent;
R3 is a thymine nucleotide (T) or a uracil nucleotide (U);
R4 is a naphthyl-uracil nucleotide (P) or a benzyl-uracil nucleotide (Z);
R5 is a cytosine nucleotide (C) or absent;

R6 is a guanine nucleotide (G) or an adenine nucleotide (A);

R7 is an adenine nucleotide (A) or absent;

R8 is a cytosine nucleotide (C) or absent;

R9 is a cytosine nucleotide (C) or an adenine nucleotide (A);

R10 is a naphthyl-uracil nucleotide (P) or a benzyl-uracil nucleotide (Z);

R11 is an adenine nucleotide (A) or a naphthyl-uracil nucleotide (P); and

R12 is a cytosine nucleotide (C) or absent, wherein the term 'absent' indicates a site from which the nucleotide is removed or a linker.

2. The insulin receptor aptamer according to claim 1, wherein, in General Formula 1, R6 is a guanine nucleotide (G), R9 is an adenine nucleotide (A), R11 is a naphthyl-uracil nucleotide (P), and R12 is a cytosine nucleotide (C).

3. The insulin receptor aptamer according to claim 2, wherein, in General Formula 1, R4 is a benzyl-uracil nucleotide (Z).

4. The insulin receptor aptamer according to claim 2, wherein, in General Formula 1, R10 is a naphthyl-uracil nucleotide (P).

5. The insulin receptor aptamer according to claim 1, wherein at least one of R1, R2, and R12 of General Formula 1 is a site from which a nucleotide is removed.

6. The insulin receptor aptamer according to claim 1, wherein at least one of R5, R7, and R8 of General Formula 1 is a linker.

7. The insulin receptor aptamer according to claim 2, wherein at least one of R1, R2, R5, and R12 of General Formula 1 is absent.

8. The insulin receptor aptamer according to claim 1, wherein the insulin receptor aptamer comprises one of the nucleotide sequences of SEQ ID NOS: 6 to 10.

9. The insulin receptor aptamer according to claim 1, wherein at least one selected from the group consisting of polyethylene glycol (PEG), biotin, inverted deoxythymidine (idT), locked nucleic acid (LNA), a methoxy group, an amino group, a fluoro group, an amine linker, a thiol linker, and cholesterol binds to at least one nucleotide comprised in the insulin receptor aptamer.

10. The insulin receptor aptamer according to claim 9, wherein a methoxy group binds to at least one nucleotide selected from the group consisting of $3^{rd}$, $4^{th}$, $5^{th}$, $14^{th}$, $16^{th}$, $19^{th}$, $21^{st}$, $23^{rd}$, $27^{th}$, $30^{th}$, $31^{st}$, and $32^{nd}$ nucleotides of General Formula 1.

11. The insulin receptor aptamer according to claim 9, wherein a fluoro group binds to either one or both of 17th and 20th nucleotides of General Formula 1.

12. The insulin receptor aptamer according to claim 1, wherein the insulin receptor aptamer binds to an insulin receptor at a dissociation constant (Kd) of 0.1 nM to 5 nM.

13. The insulin receptor aptamer according to claim 1, wherein the insulin receptor aptamer phosphorylates Y1150 of the insulin receptor.

14. The insulin receptor aptamer according to claim 1, wherein the insulin receptor aptamer is present as a dimer or a multimer.

15. An insulin receptor agonist comprising the insulin receptor aptamer according to claim 1.

16. A pharmaceutical composition for preventing or treating an insulin-related disease, comprising the insulin receptor aptamer according to claim 1 as an active ingredient, wherein the composition further comprises a pharmaceutically acceptable carrier, an excipient or a diluent.

17. A method of preventing or treating an insulin-related disease, the method comprising administering the pharmaceutical composition according to claim 16 to a subject except a human.

18. A composition for diagnosing diabetes or diabetic complications comprising the insulin receptor aptamer according to claim 1 as an active ingredient.

19. The method of claim 17, wherein the insulin-related disease is diabetes, diabetic complications, metabolic syndromes, obesity, or cardiovascular diseases.

* * * * *